US011103448B2

(12) United States Patent
Morton et al.

(10) Patent No.: US 11,103,448 B2
(45) Date of Patent: Aug. 31, 2021

(54) MANUFACTURE OF PHARMACEUTICAL COMPOSITIONS

(71) Applicant: VECTURA LIMITED, Chippenham (GB)

(72) Inventors: David Morton, Chippenham (GB); John Staniforth, Chippenham (GB)

(73) Assignee: VECTURA LIMITED, Chippenham (GB)

( * ) Notice: Subject to any disclaimer, the term of this patent is extended or adjusted under 35 U.S.C. 154(b) by 0 days.

(21) Appl. No.: 15/903,345

(22) Filed: Feb. 23, 2018

(65) Prior Publication Data

US 2018/0177721 A1 Jun. 28, 2018

Related U.S. Application Data

(63) Continuation of application No. 14/970,261, filed on Dec. 15, 2015, now abandoned, which is a continuation of application No. 13/337,596, filed on Dec. 27, 2011, now abandoned, which is a continuation of application No. 10/571,146, filed as application No. PCT/GB2004/003996 on Sep. 15, 2004, now Pat. No. 8,182,838.

(30) Foreign Application Priority Data

Sep. 15, 2003 (GB) ..................................... 0321607

(51) Int. Cl.
| | |
|---|---|
| *A61K 9/00* | (2006.01) |
| *A61K 9/16* | (2006.01) |
| *A61K 9/50* | (2006.01) |
| *A61K 31/55* | (2006.01) |
| *B02C 19/06* | (2006.01) |
| *A61K 31/473* | (2006.01) |
| *A61K 31/5513* | (2006.01) |
| *A61K 31/727* | (2006.01) |

(52) U.S. Cl.
CPC ............ *A61K 9/0075* (2013.01); *A61K 9/008* (2013.01); *A61K 9/16* (2013.01); *A61K 9/1617* (2013.01); *A61K 9/1623* (2013.01); *A61K 9/1694* (2013.01); *A61K 9/50* (2013.01); *A61K 31/473* (2013.01); *A61K 31/55* (2013.01); *A61K 31/5513* (2013.01); *A61K 31/727* (2013.01); *B02C 19/06* (2013.01)

(58) Field of Classification Search
CPC ...... A61K 9/0075; A61K 9/16; A61K 9/1617; A61K 9/1623; A61K 9/50; A61K 9/008; B02C 19/06
See application file for complete search history.

(56) References Cited

U.S. PATENT DOCUMENTS

| | | | | |
|---|---|---|---|---|
| 4,374,082 A | | 2/1983 | Hochschild | |
| 4,895,726 A | | 1/1990 | Curtet et al. | |
| 5,747,002 A | * | 5/1998 | Clark | A61K 9/0075 424/45 |
| 6,153,224 A | * | 11/2000 | Staniforth | A61K 9/0075 424/490 |
| 6,475,523 B1 | | 11/2002 | Staniforth | |
| 6,989,155 B1 | * | 1/2006 | Ganderton | A61K 9/145 424/499 |
| 7,541,022 B2 | | 6/2009 | Staniforth et al. | |
| 7,736,670 B2 | | 6/2010 | Staniforth et al. | |
| 7,744,855 B2 | | 6/2010 | Staniforth et al. | |
| 8,048,451 B2 | | 11/2011 | Staniforth et al. | |
| 8,101,160 B2 | | 1/2012 | Staniforth et al. | |
| 8,182,838 B2 | | 5/2012 | Morton et al. | |
| 8,303,991 B2 | | 11/2012 | Staniforth et al. | |
| 8,871,274 B2 | | 10/2014 | Staniforth et al. | |
| 8,956,661 B2 | | 2/2015 | Staniforth et al. | |
| 9,351,928 B2 | | 5/2016 | Staniforth et al. | |
| 9,585,834 B2 | | 3/2017 | Morton | |
| 9,642,800 B2 | | 5/2017 | Morton | |
| 9,931,304 B2 | * | 4/2018 | Staniforth | A61K 9/0075 |
| 9,962,338 B2 | * | 5/2018 | Staniforth | A61K 9/0075 |
| 2003/0162835 A1 | | 8/2003 | Staniforth | |
| 2003/0165436 A1 | | 9/2003 | Staniforth | |
| 2003/0175214 A1 | | 9/2003 | Staniforth | |
| 2003/0185764 A1 | | 10/2003 | Staniforth | |
| 2004/0018989 A1 | | 1/2004 | Jackson et al. | |
| 2004/0037785 A1 | | 2/2004 | Staniforth | |
| 2004/0047810 A1 | | 3/2004 | Staniforth | |
| 2004/0067920 A1 | * | 4/2004 | Leonard | A61K 9/0075 514/178 |
| 2004/0071635 A1 | | 4/2004 | Staniforth | |
| 2004/0121003 A1 | | 6/2004 | Chickering | |
| 2005/0079138 A1 | | 4/2005 | Chickering | |
| 2005/0152849 A1 | | 7/2005 | Staniforth | |

(Continued)

FOREIGN PATENT DOCUMENTS

| | | |
|---|---|---|
| DE | 10061932 | 10/2002 |
| DE | 10061932 A1 | 10/2002 |

(Continued)

OTHER PUBLICATIONS

Peart J. et al. "Multicomponent Particle Interactions in Dry Powder Aerosols." Pharmaceutical Research, Spring New York LLC, US, vol. 14, No. 11-S, Jan. 1, 1997, pp. S142-S143, XP001030455.

(Continued)

*Primary Examiner* — Mina Haghighatian
(74) *Attorney, Agent, or Firm* — Barnes & Thornburg LLP; Ryan P. Cox

(57) ABSTRACT

The present invention relates to particles and to methods of making particles. In particular, the invention relates to methods of making composite active particles comprising a pharmaceutically active material for pulmonary inhalation, the method comprising a jet milling process.

15 Claims, 5 Drawing Sheets

(56) References Cited

U.S. PATENT DOCUMENTS

| | | | |
|---|---|---|---|
| 2006/0292081 A1 | 3/2006 | Morton et al. |
| 2006/0093677 A1 | 5/2006 | Chickering |
| 2006/0093678 A1 | 5/2006 | Chickering |
| 2006/0147389 A1 | 7/2006 | Staniforth |
| 2006/0175214 A1 | 8/2006 | Conklin |
| 2006/0257491 A1 | 11/2006 | Morton et al. |
| 2007/0081948 A1 | 4/2007 | Morton |
| 2008/0127972 A1 | 6/2008 | Morton |
| 2015/0079185 A1 | 3/2015 | Staniforth et al. |
| 2016/0243046 A1 | 8/2016 | Staniforth et al. |
| 2017/0216203 A1 | 8/2017 | Morton |

FOREIGN PATENT DOCUMENTS

| | | | |
|---|---|---|---|
| EP | 1048295 | | 11/2000 |
| EP | 1048295 A2 | | 11/2000 |
| EP | 1337240 | | 8/2003 |
| GB | WO 0033811 | * | 6/2000 |
| WO | 199623485 | | 8/1996 |
| WO | 199703649 | | 2/1997 |
| WO | 200061108 | | 10/2000 |
| WO | 200178693 | | 10/2001 |
| WO | 2001089492 | | 11/2001 |
| WO | WO2001/089492 A1 | | 11/2001 |
| WO | 200200197 | | 1/2002 |
| WO | 200243701 | | 6/2002 |
| WO | 20020243700 | | 6/2002 |
| WO | 2004060344 | | 7/2004 |
| WO | 2004089374 | | 10/2004 |
| WO | WO2004/089374 A1 | | 10/2004 |
| WO | 2004093848 | | 11/2004 |
| WO | WO2004/093848 A2 | | 11/2004 |

OTHER PUBLICATIONS

Kawaskima et al. "Design of inhalation dry powder of pranlukast hydrate to improve dispersibility by the surface modification with light anhydrous silicic acid (Aerosil 200)." International Journal of Pharmaceutics, vol. 173, No. 1-2, Oct. 1, 1998, pp. 243-251, XP0551909780.

Banker et al., "Modern Pharmaceutics" Marcel Dekker 2002.

Hickey "Lung Deposition and Clearance of Pharmaceutical Aerosols: What Can be Learned from Inhalation Toxicology and Industrial Hygiene" Aerosol Science and Technology, 1993.

Gennaro, "Remington: The Science and Practice of Pharmacy" Lippincott, Williams and Wilkins, 2000.

Malcolmson et al, "Dry powder formulations for pulmonary delivery" PSTT, 1998.

Labiris et al, "Pulmonary drug delivery. Part II: The role of inhalant delivery devices and drug formulations in therapeutic effectiveness of aerosolized medications." British Journal of Clinical Pharmacology, Aug. 20, 2003.

Zeng et al., "Particulate Interactions in Dry Powder Formulations for Inhalation" Taylor & Francis, 2001.

Byron et al., "Optimized Inhalation Aerosols I. The Effects of Spherical Baffle Size and Position upon the Output of Several Pressurized Nonaqueous Suspension Formulations" Pharmaceutical Research 1989.

Weast, "Handbook of Chemistry and Physics" CRC Press, 1973.

Patient Packet Insert, Triglide, Food and Drug Administration, Feb. 2007.

International Search Report, dated Mar. 18, 2005, issued by the European Patent Office in connection with corresponding International Application No. PCT/GB2004/003996.

Modern Pharmaceutics, Fourth Edition, Revised and Expanded, Eds. G.S. Banker and C.T. Rhodes, Drugs and the Pharmaceutical Sciences, 2002.

A.J. Hickey, Aerosol Science and Technology, 1993, 18, 290-304.

Remington: The Science and Practice of Pharmacy, 20th Edition, Ed. A.R. Gennaro, Lippincott, Williams and Wilkins, 2000, pp. 681-685.

R.J. Malcomson and J.K. Embleton, PSTT, 1998, 1(9), 394-398.

N.R. Labiris and M.B. Dolovich, Br. J. Clin. Pharmacol., 2003, 56, 600-612.

Printout from the Wiley website showing details of the N.R. Labiris et al. document.

P.R. Byron et al., Pharm. Res., 1989, 6, 225-230.

X.-M. Zeng et al Particle interactions in dry powder formulations for inhalation, Taylor & Francis, London and New York, 2001, pp. 133-138.

Fee, J. Valerie, et al. "Influence of Hydrophobic Material on Dissolution of a Nondisintegrating Hydophilic Solid (Potassium Chloride)," Journal of Pharmaceutical Science, vol. 65, No. 2, p. 182-187 (Feb. 1976).

* cited by examiner d(0.5) 2.8μm    d(0.9) 6.3μm    D[4,3] 3.3μm d(0.5) 1.4μm    d(0.9) 2.9μm    D[4,3] 1.6μm d(0.5) 2.6μm          d(0.9) 5.2μm          D[4,3] 2.9μm d(0.5) 2.5μm          d(0.9) 4.2μm          D[4,3] 2.6μm d(0.5) 1.1μm        d(0.9) 2.6μm        D[4,3] 1.4μm d(0.5) 1.2μm        d(0.9) 2.5μm        D[4,3] 1.4μm d(0.5) 1.8μm  d(0.9) 243.6μm  D[4,3] 38.0μm d(0.5) 1.6μm  d(0.9) 261.0μm  D[4,3] 55.8μm

MANUFACTURE OF PHARMACEUTICAL COMPOSITIONS

RELATED APPLICATIONS

This application is a continuation of U.S. application Ser. No. 14/970,261, filed Dec. 15, 2015, which is a continuation of U.S. application Ser. No. 13/337,596 filed Dec. 27, 2011, which is a continuation of U.S. application Ser. No. 10/571,146 filed Jul. 17, 2006, now patented as U.S. Pat. No. 8,182,838 which issued May 22, 2012, which is a United States national stage of International Application No. PCT/GB2004/003996, filed Sep. 15, 2004, which was published as International Publication No. WO 2005/025536, and which claims benefit of United Kingdom Application No. 0321607.4 filed, Sep. 15, 2003, the entire contents of which are hereby expressly incorporated herein by reference thereto.

The present invention relates to particles and to methods of making particles. In particular, the invention relates to methods of making composite particles comprising a pharmaceutically active material and an additive material, for pulmonary inhalation, the methods comprising a co-jet milling process.

The lung provides an obvious target for local administration of formulations which are intended to cure or alleviate respiratory or pulmonary diseases, such as cystic fibrosis (CF), asthma, lung cancer, etc. The lung also provides a route for delivery of systemically acting formulations to the blood stream, for example, for delivery of active agents which are not suitable for oral ingestion, such as agents that degrade in the digestive tract before they can be absorbed, and those requiring an extremely rapid onset of their therapeutic action.

It is known to administer pharmaceutically active agents to a patient in the form of fine, dry particles (active particles), for example, by pulmonary administration of a particulate medicament composition which is inhaled by the patient. Known devices for the administration of drugs to the respiratory system include pressurised metered dose inhalers (pMDIs) and dry powder inhalers (DPIs).

The size of the active particles is of great importance in determining the site of the absorption in the lung. In order for the particles be carried deep into the lungs, the particles must be very fine, for example having a mass median aerodynamic diameter (MMAD) of less than 10 μm. Particles having aerodynamic diameters greater than about 10 μm are likely to impact the walls of the throat and generally do not reach the lung. Particles having aerodynamic diameters in the range of about 5 μm to about 2 μm will generally be deposited in the respiratory bronchioles whereas smaller particles having aerodynamic diameters in the range of about 3 to about 0.05 μm are likely to be deposited in the alveoli and to be absorbed into the bloodstream.

Fine particles, that is those with an MMAD of less than about 10 μm tend to be increasingly thermodynamically unstable due to their high surface area to volume ratio, which provides an increasing surface free energy with this decreasing particle size, and consequently increases the tendency of particles to agglomerate and the strength of the agglomerate. In the inhaler, agglomeration of fine particles and adherence of such particles to the walls of the inhaler are problems that result in the fine particles leaving the inhaler as large, stable agglomerates, or being unable to leave the inhaler and remaining adhered to the interior of the device, or even clogging or blocking the inhaler.

The uncertainty as to the extent of formation of stable agglomerates of the particles between each actuation of the inhaler, and also between different inhalers and different batches of particles, leads to poor dose reproducibility. Furthermore, the formation of agglomerates means that the MMAD of the active particles can be vastly increased, with agglomerates of the active particles not reaching the required part of the lung.

The metered dose (MD) of a dry powder formulation is the total mass of active agent present in the metered form presented by the inhaler device in question. For example, the MD might be the mass of active agent present in a capsule for a Cyclohaler (trade mark), or in a foil blister in an Aspirair (trade mark) device.

The emitted dose (ED) is the total mass of the active agent emitted from the device following actuation. It does not include the material left inside or on the surfaces of the device. The ED is measured by collecting the total emitted mass from the device in an apparatus frequently referred to as a dose uniformity sampling apparatus (DUSA), and recovering this by a validated quantitative wet chemical assay.

The fine particle dose (FPD) is the total mass of active agent which is emitted from the device following actuation which is present in an aerodynamic particle size smaller than a defined limit This limit is generally taken to be Si.tm if not expressly stated to be an alternative limit, such as 3 pm or 1 μm, etc. The FPD is measured using an impactor or impinger, such as a twin stage impinger (TSI), multi-stage liquid impinger (MSLI), Andersen Cascade Impactor (ACI) or a Next Generation Impactor (NGI). Each impactor or impinger has a pre-determined aerodynamic particle size collection cut-off point for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

The fine particle fraction (FPF) is normally defined as the FPD divided by the ED and expressed as a percentage. Herein, the FPF of ED is referred to as FPF(ED) and is calculated as FPF(ED)=(FPD/ED)×100%.

The fine particle fraction (FPF) may also be defined as the FPD divided by the MD and expressed as a percentage. Herein, the FPF of MD is referred to as FPF(MD), and is calculated as FPF(MD)=(FPD/MD)×100%.

The terms "delivered dose" or "DD" and "emitted dose" or "ED" are used interchangeably herein. These are measured as set out in the current EP monograph for inhalation products.

"Actuation of an inhaler" refers to the process during which a dose of the powder is removed from its rest position in the inhaler. That step takes place after the powder has been loaded into the inhaler ready for use.

The tendency of fine particles to agglomerate means that the FPF of a given dose can be highly unpredictable and a variable proportion of the fine particles will be administered to the lung, or to the correct part of the lung, as a result. This is observed, for example, in formulations comprising pure drug in fine particle form. Such formulations exhibit poor flow properties and poor FPF.

In an attempt to improve this situation and to provide a consistent FPF and FPD, dry powder formulations often include additive material.

The additive material is intended to reduce the adhesion and cohesion experienced by the particles in the dry powder formulation. It is thought that the additive material interferes with the weak bonding forces between the small particles, helping to keep the particles separated and reducing the adhesion of such particles to one another, to other particles in the formulation if present and to the internal surfaces of the inhaler device. Where agglomerates of particles are formed, the addition of particles of additive material decreases the stability of those agglomerates so that they are more likely to break up in the turbulent air stream and collisions created on actuation of the inhaler device, whereupon the particles are expelled from the device and inhaled. As the agglomerates break up, the active particles may return to the form of small individual particles or agglomerates of small numbers of particles which are capable of reaching the lower lung.

In the prior art, dry powder formulations are discussed which include distinct particles of additive material (generally of a size comparable to that of the fine active particles). In some embodiments, the additive material may form a coating, generally a discontinuous coating, on the active particles and/or on any carrier particles.

Preferably, the additive material is an anti-adherent material and it will tend to reduce the cohesion between particles and will also prevent fine particles becoming attached to the inner surfaces of the inhaler device. Advantageously, the additive material is an anti-friction agent or glidant and will give the powder formulation better flow properties in the inhaler. The additive materials used in this way may not necessarily be usually referred to as anti-adherents or anti-friction agents, but they will have the effect of decreasing the adhesion and cohesion between the particles or improving the flow of the powder. The additive materials are sometimes referred to as force control agents (FCAs) and they usually lead to better dose reproducibility and higher FPFs.

Therefore, an additive material or FCA, as used herein, is a material whose presence on the surface of a particle can modify the adhesive and cohesive surface forces experienced by that particle, in the presence of other particles and in relation to the surfaces that the particles are exposed to. In general, its function is to reduce both the adhesive and cohesive forces.

The reduced tendency of the particles to bond strongly, either to each other or to the device itself, not only reduces powder cohesion and adhesion, but can also promote better flow characteristics. This leads to improvements in the dose reproducibility because it reduces the variation in the amount of powder metered out for each dose and improves the release of the powder from the device. It also increases the likelihood that the active material, which does leave the device, will reach the lower lung of the patient.

It is favourable for unstable agglomerates of particles to be present in the powder when it is in the inhaler device. As indicated above, for a powder to leave an inhaler device efficiently and reproducibly, the particles of such a powder should be large, preferably larger than about 40 µm. Such a powder may be in the form of either individual particles having a size of about 40 µm or larger and/or agglomerates of finer particles, the agglomerates having a size of about 40 µm or larger. The agglomerates formed can have a size of as much as about 100 µm and, with the addition of the additive material, those agglomerates are more likely to be broken down efficiently in the turbulent airstream created on inhalation. Therefore, the formation of unstable agglomerates of particles in the powder may be favoured compared with a powder in which there is substantially no agglomeration.

The reduction in the cohesion and adhesion between the active particles can lead to equivalent performance with reduced agglomerate size, or even with individual particles.

In a further attempt to improve extraction of the dry powder from the dispensing device and to provide a consistent FPF and FPD, dry powder formulations often include coarse carrier particles of excipient material mixed with fine particles of active material. Rather than sticking to one another, the fine active particles tend to adhere to the surfaces of the coarse carrier particles whilst in the inhaler device, but are supposed to release and become dispersed upon actuation of the dispensing device and inhalation into the respiratory tract, to give a fine suspension. The carrier particles preferably have MMADs greater than about 60 µm.

The inclusion of coarse carrier particles is also very attractive where very small doses of active agent are dispensed. It is very difficult to accurately and reproducibly dispense very small quantities of powder and small variations in the amount of powder dispensed will mean large variations in the dose of active agent where the powder comprises mainly active particles.

Therefore, the addition of a diluent, in the form of large excipient particles will make dosing more reproducible and accurate.

Carrier particles may be of any acceptable excipient material or combination of materials. For example, the carrier particles may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles comprise a polyol. In particular, the carrier particles may be particles of crystalline sugar, for example mannitol, dextrose or lactose. Preferably, the carrier particles are composed of lactose.

However, a further difficulty is encountered when adding coarse carrier particles to a composition of fine active particles and that difficulty is ensuring that the fine particles detach from the surface of the large particles upon actuation of the delivery device.

The step of dispersing the active particles from other active particles and from carrier particles, if present, to form an aerosol of fine active particles for inhalation is significant in determining the proportion of the dose of active material which reaches the desired site of absorption in the lungs. In order to improve the efficiency of that dispersal, it is known to include in the composition additive materials of the nature discussed above. Compositions comprising fine active particles and additive materials are disclosed in WO 97/03649 and WO 96/23485.

It is an aim of the present invention to provide a method of producing dry powder compositions which have physical and chemical properties which lead to an enhanced FPF and FPD. This will lead to greater dosing efficiency, with a greater proportion of the active agent being dispensed and reaching the desired part of the lung for achieving the required therapeutic effect.

It is also an aim of the present invention to provide a method of producing powders wherein the method achieves a further reduction in the size of the active particles, preferably so that the particles are of an appropriate size for administration to the deep lung by inhalation. Preferably, this is possible using both active dry powder inhaler devices and passive dry powder inhaler devices.

In particular, the present invention seeks to optimise the preparation of particles of active agent used in the dry powder composition by engineering the particles making up the dry powder composition and, in particular, by engineering the particles of active agent. It is proposed to do this by adjusting and adapting the milling process used to form the particles of active agent.

According to a first aspect of the present invention, a method is provided for making composite active particles for use in a pharmaceutical composition for pulmonary inhalation, the method comprising jet milling active particles in the presence of additive material, preferably wherein the jet milling is conducted using air or a compressible gas or fluid. Preferably, the additive material is a force control agent, as defined herein.

Figure 1:
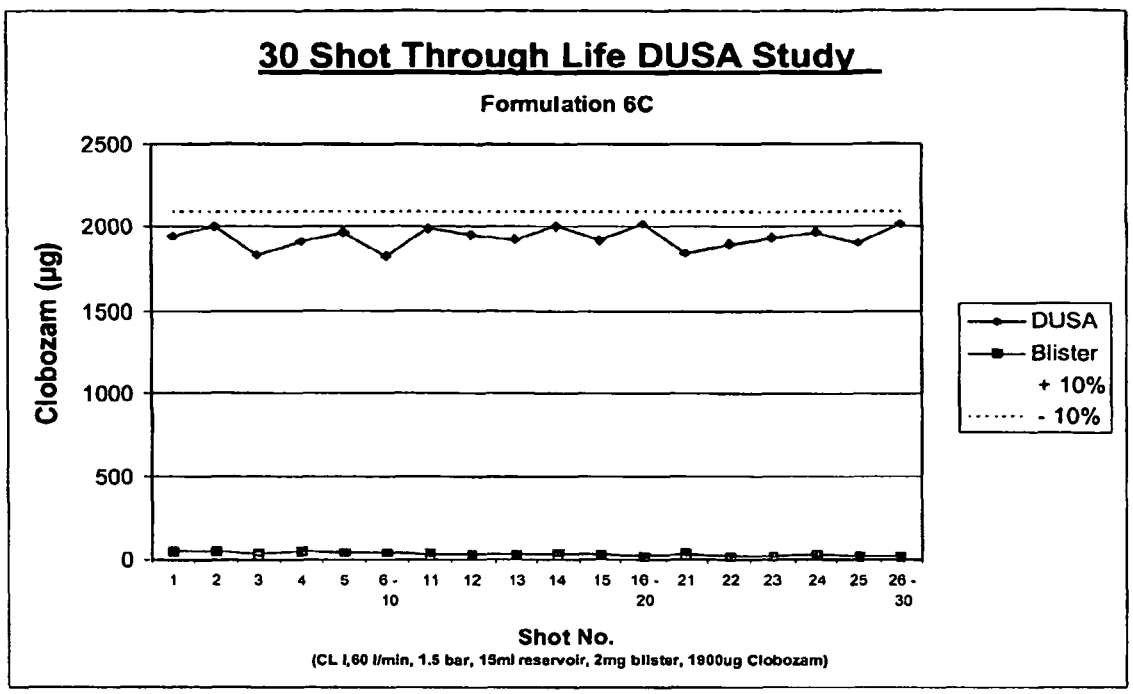
FIG. 1 is a graph presenting the life dose uniformity for formulation "6C".

In the conventional use of the word, "milling" means the use of any mechanical process which applies sufficient force to the particles of active material that it is capable of breaking coarse particles (for example, particles with an MMAD greater than 100 pm) down to fine particles (for example, having an MMAD not more than 50 µm). In the present invention, the term "milling" also refers to deagglomeration of particles in a formulation, with or without particle size reduction. The particles being milled may be large or fine prior to the milling step.

In the prior art, co-milling or co-micronising active agents and additive materials have been suggested. It is stated that milling can be used to substantially decrease the size of particles of active agent. However, if the particles of active agent are already fine, for example have an MMAD of less than 20 µm prior to the milling step, the size of those particles may not be significantly reduced where the milling of these active particles takes place in the presence of an additive material. Rather, milling of fine active particles with additive particles using the methods described in the prior art (for example, in WO 02/43701) will result in the additive material becoming deformed and being smeared over or fused to the surfaces of the active particles. The resultant composite active particles have been found to be less cohesive after the milling treatment. However, there is still the disadvantage that this is not combined with a significant reduction in the size of the particles.

The prior art mentions two types of processes in the context of co-milling or co-micronising active and additive particles.

First, there is the compressive type process, such as mechanofusion, cyclomixing and similar methods. As the name suggests, mechanofusion is a dry coating process designed to mechanically fuse a first material onto a second material. The first material is generally smaller and/or softer than the second. The mechanofusion and cyclomixing working principles are distinct from alternative milling techniques in having a particular interaction between an inner element and a vessel wall, and are based on providing energy by a controlled and substantial compressive force. The term mechanofusion is used here to encompass any process which operates in such a manner, and applies in a rotational vessel a controlled and substantial compressive force. "Food processor" type mixers are not considered useful for the processes required in the present invention. Such mixers do not provide the necessary compressive forces. They include conventional mixing blades and these are not arranged with a small enough gap between the blades and the vessel wall.

When fine active particles and additive particles are fed into the mechanofusion driven vessel (such as a Mechano-Fusion system (Hosokawa Micron Ltd)), they are subject to a centrifugal force and are pressed against the vessel inner wall. The powder is compressed between the fixed clearance of the drum wall and an inner element with high relative speed between drum and element. The inner wall and the element together form a gap or nip in which the particles are pressed together. As a result, the particles experience very high shear forces and very strong compressive stresses as they are trapped between the inner drum wall and the inner element. The particles are pressed against each other with enough energy to locally heat and soften, break, distort, flatten and wrap the additive particles around the core particle to form a coating. The energy is generally sufficient to break up agglomerates and some degree of size reduction of both components may occur.

These mechanofusion and cyclomixing processes apply a high enough degree of force to separate the individual particles of active material and to break up tightly bound agglomerates of the active particles such that effective mixing and effective application of the additive material to the surfaces of those particles is achieved. An especially desirable aspect of the described co-milling processes is that the additive material becomes deformed in the milling and may be smeared over or fused to the surfaces of the active particles.

However, in practice, this compression process produces little or no milling (i.e. size reduction) of the drug particles, especially where they are already in a micronised form (i.e. <10 µm), the only physical change which may be observed is a plastic deformation of the particles to a rounder shape.

Secondly, there are the impact milling processes involved in ball milling and the use of a homogenizer.

Ball milling is a suitable milling method for use in the prior art co-milling processes. Centrifugal and planetary ball milling are especially preferred methods. Alternatively, a high pressure homogeniser may be used in which a non-compressible fluid containing the particles is forced through a valve at high pressure producing conditions of high shear and turbulence. Such homogenisers may be more suitable than ball mills for use in large scale preparations of the composite active particles.

Suitable homogensiers include EmulsiFlex high pressure homogenisers which are capable of pressures up to 4000 bar, Niro Soavi high pressure homogenisers (capable of pressures up to 2000 bar), and Microfluidics Microfluidisers (capable of pressures up to 2750 bar). The milling step may, alternatively, involve a high energy media mill or an agitator bead mill, for example, the Netzsch high energy media mill, or the DYNO-mill (Willy A. Bachofen AG, Switzerland).

These processes create high-energy impacts between media and particles or between particles. In practice, while these processes are good at making very small particles, it has been found that neither the ball mill nor the homogenizer was effective in producing dispersion improvements in resultant drug powders in the way observed for the compressive process. It is believed that the second impact processes are not as effective in producing a coating of additive material on each particle.

Conventional methods comprising co-milling active material with additive materials (as described in WO 02/43701) result in composite active particles which are fine particles of active material with an amount of the additive material on their surfaces. The additive material is preferably in the form of a coating on the surfaces of the particles of active material. The coating may be a discontinuous coating. The additive material may be in the form of particles adhering to the surfaces of the particles of active material.

At least some of the composite active particles may be in the form of agglomerates. However, when the composite active particles are included in a pharmaceutical composition, the additive material promotes the dispersal of the composite active particles on administration of that composition to a patient, via actuation of an inhaler.

Jet mills are capable of reducing solids to particle sizes in the low-micron to submicron range. The grinding energy is created by gas streams from horizontal grinding air nozzles. Particles in the fluidized bed created by the gas streams are accelerated towards the centre of the mill, colliding with slower moving particles. The gas streams and the particles carried in them create a violent turbulence and as the particles collide with one another they are pulverized.

In the past, jet milling has not been considered attractive for co-milling active and additive particles, processes like mechanofusion and cyclomixing or equivalent being clearly preferred. The collisions between the particles in a jet mill are somewhat uncontrolled and those skilled in the art, therefore, considered it unlikely for this technique to be able to provide the desired deposition of a coating of additive material on the surface of the active particles. Moreover, it was believed that, unlike the situation with mechanofusion, cyclomixing and similar processes, segregation of the powder constituents occurred in jet mills, such that the finer particles, that were believed to be the most effective, could escape from the process. In contrast, it could be clearly envisaged how techniques such as mechanofusion would result in the desired coating.

It should also be noted that it was also previously believed that the compressive or impact milling processes must be carried out in a closed system, in order to prevent segregation of the different particles. This has also been found to be untrue and the co jet milling processes according to the present invention do not need to be carried out in a closed system. Even in an open system, the co-jet milling has surprisingly been found not to result in the loss of the small particles, even when using leucine as the additive material.

It has now unexpectedly been discovered that composite particles of active and additive material can be produced by co-jet milling these materials. The resultant particles have excellent characteristics which lead to greatly improved performance when the particles are dispensed from a DPI for administration by inhalation. In particular, co jet milling active and additive particles can lead to further significant particle size reduction. What is more, the composite active particles exhibit an enhanced FPD and FPF, compared to those disclosed in the prior art.

The effectiveness of the promotion of dispersal of active particles has been found to be enhanced by using the co jet milling methods according to the present invention in comparison to compositions which are made by simple blending of similarly sized particles of active material with additive material. The phrase "simple blending" means blending or mixing—using conventional tumble blenders or high shear mixing and basically the use of traditional mixing apparatus which would be available to the skilled person in a standard laboratory.

It has been found that, contrary to previous belief, co-jet milling can be used to produce sufficiently complete coatings of additive material, which have now been observed to substantially improve the dispersion of the powders from an inhaler. The jet milling process can also be adjusted to tailor the composite particles to the type of inhaler device to be used to dispense the particles. The inhaler device may be an active inhaler device, such as Aspirair (trade mark) or it may be a passive device.

Further, the co-jet milling process may optionally also be arranged so as to significantly mill the active particles, that is, to significantly reduce the size of the active particles: The co-jet milling of the present invention may even, in certain circumstances, be more efficient in the presence of the additive material than it is in the absence of the additive material. The benefits are that it is therefore possible to produce smaller particles for the same mill, and it is possible to produce milled particles with less energy. Co-jet milling should also reduce the problem of amorphous content by both creating less amorphous material, as well as hiding it below a layer of additive material.

The impact forces of the co-jet milling are sufficient to break up agglomerates of drug, even micronised drug, and are effective at distributing the additive material to the consequently exposed faces of the particles. This is an important aspect of the present invention. It has been shown that if the energy of the process is not sufficient to break up the agglomerates of drug (for example, as will be the case when one uses a conventional blender), the additive material merely coats the agglomerates and these agglomerates can even be compressed, making them even more difficult to disperse. This is clearly undesirable when one is seeking to prepare a dry powder for administration by inhalation.

Fine particles of active material suitable for pulmonary administration have often been prepared by milling in the past. However, when using many of the known milling techniques, once the particles reach a minimum size, referred to as the "critical size", they tend to re-combine at the same rate as being fractured, or do not fracture effectively and therefore no further reduction in the particle size is achieved. Critical sizes are specific to particular mills and sets of milling conditions.

Thus, manufacture of fine particles by milling can require much effort and there are factors which consequently place limits on the minimum size of particles of active material which can be achieved, in practice, by such milling processes.

The present invention consequently relates to the provision of a high-energy impact process that is effective in producing improvements in the resultant drug powders.

Furthermore, contrary to conventional thinking, the processes of the present invention do not need to be carried out in a closed system. Even where the additive material being co-jet milled is leucine, there is no observed loss of additive material or reduction in coating where the jet milling is not carried out in a closed system. Rather, in one embodiment of the invention, the method of the present invention is carried out in a flow-through system, without any loss in performance of the resultant composite particles. This is an economically important feature, as it can significantly increase the rate of production of the powders of the invention.

In one embodiment of the present invention, 90% by mass of the active particles jet-milled are initially less than 20 pm in diameter. More preferably, 90% by mass of the active particles jet-milled are initially less than 10 pm in diameter, and most preferably less than 5 μm in diameter.

In another embodiment, 90% by mass of the additive particles jet-milled are initially less than 20 pm in diameter. More preferably, 90% by mass of the additive particles jet-milled are initially less than 10 μm in diameter, and most preferably less than 5 pm in diameter or less than 3 pm in diameter.

The terms "active particles" and "particles of active material" and the like are used interchangeably herein. The active particles comprise one or more pharmaceutically active agents. The preferred active agents include:

1) steroid drugs such as alcometasone, beclomethasone, beclomethasone dipropionate, betamethasone, budesonide, clobetasol, deflazacort, diflucortolone, desoxymethasone, dexamethasone, fludrocortisone, flunisolide, fluocinolone, fluometholone, fluticasone, fluticasone proprionate, hydrocortisone, triamcinolone, nandrolone decanoate, neomycin sulphate, rimexolone, methylprednisolone and prednisolone;

2) antibiotic and antibacterial agents such as metronidazole, sulphadiazine, triclosan, neomycin, amoxicillin, amphotericin, clindamycin, aclarubicin, dactinomycin, nystatin, mupirocin and chlorhexidine;

3) systemically active drugs such as isosorbide dinitrate, isosorbide mononitrate, apomorphine and nicotine;

4) antihistamines such as azelastine, chlorpheniramine, astemizole, cetirizine, cinnarizine, desloratadine, loratadine, hydroxyzine, diphenhydramine, fexofenadine, ketotifen, promethazine, trimeprazine and terfenadine;

5) anti-inflammatory agents such as piroxicam, nedocromil, benzydamine, diclofenac sodium, ketoprofen, ibuprofen, heparinoid, nedocromil, cromoglycate, fasafungine and iodoxamide;

6) anticholinergic agents such as atropine, benzatropine, biperiden, cyclopentolate, oxybutinin, orphenadine hydrochloride, glycopyrronium, glycopyrrolate, procyclidine, propantheline, propiverine, tiotropium, tropicamide, trospium, ipratropium bromide and oxitroprium bromide;

7) anti-emetics such as bestahistine, dolasetron, nabilone, prochlorperazine, ondansetron, trifluoperazine, tropisetron, domperidone, hyoscine, cinnarizine, metoclopramide, cyclizine, dimenhydrinate and promethazine;

8) hormonal drugs such as protirelin, thyroxine, salcotonin, somatropin, tetracosactide, vasopressin or desmopressin;

9) bronchodilators such as salbutamol, fenoterol and salmeterol;

10) sympathomimetic drugs such as adrenaline, noradrenaline, dexamfetamine, dipirefin, dobutamine, dopexamine, phenylephrine, isoprenaline, dopamine, pseudoephedrine, tramazoline and xylometazoline;

11) anti-fungal drugs such as amphotericin, caspofungin, clotrimazole, econazole nitrate, fluconazole, ketoconazole, nystatin, itraconazole, terbinafine, voriconazole and miconazole;

12) local anaesthetics such as amethocaine, bupivacaine, hydrocortisone, methylprednisolone, prilocaine, proxymetacaine, ropivacaine, tyrothricin, benzocaine and lignocaine;

13) opiates, preferably for pain management, such as buprenorphine, dextromoramide, diamorphine, codeine phosphate, dextropropoxyphene, dihydrocodeine, papaveretum, pholcodeine, loperamide, fentanyl, methadone, morphine, oxycodone, phenazocine, pethidine and combinations thereof with an anti-emetic;

14) analgesics and drugs for treating migraine such as clonidine, codine, coproxamol, dextropropoxyene, ergotamine, sumatriptan, tramadol and non-steroidal anti-inflammatory drugs;

15) narcotic agonists and opiate antidotes such as naloxone, and pentazocine;

16) phosphodiesterase type 5 inhibitors, such as sildenafil (Viagra (trade mark));

17) antidepressants such as amesergide, amineptine, amitriptyline, amoxapine, benactyzine, brofaromine, bupropion, butriptyline, cianopramine, citalopram, clorgyline, clovoxamine, demexiptiline, desipramine, dibenzepin, dimetacrine, dothiepin, doxepin, etoperidone, femoxetine, fezolamine, fluoxetine, fluvoxamine, ifoxetine, imipramine, iprindole, iso-carboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine and zimeldine;

18) serotonin agonists such as 2-methyl serotonin, buspirone, ipsaperone, tiaspirone, gepirone, lysergic acid diethylamide, ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, trazodone, zacopride and mezacopride;

19) serotonin antagonists including ondansetron, granisetron, metoclopramide, tropisetron, dolasetron, trimethobenzamide, methysergide, risperidone, ketanserin, ritanserin, clozapine, amitryptiline, R(+)-α-(2,3-dimethoxyphenyl)-1-[2-(4-fluorophenyflethyl]-4-piperidine-methanol, azatadine, cyproheptadine, fenclonine, dexfenfluramine, fenfluramine, chlorpromazine and mianserin;

20) adrenergic agonists including methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudo-ephedrine, methylphenidate, pemoline, naphazoline, tetrahydrozoline, oxymetazoline, xylometazoline, phenylpropanolamine, phenylethyl amine, dopamine, dobutamine, colterol, isoproterenol, isotharine, metaproterenol, terbutaline, metaraminol, tyramine, hydroxyamphetamine, ritodrine, prenalterol, albuterol, isoetharine, pirbuterol, bitolterol, fenoterol, formoterol, procaterol, salmeterol, mephenterine and propylhexedrine;

21) adrenergic antagonists such as phcnoxybenzamine, phentolamine, tolazoline, prazosin, terazosin, doxazosin, trimazosin, yohimbine, ergot alkaloids, labetalol, ketanserin, urapidil, alfuzosin, bunazosin, tamsulosin, chlorpromazine, haloperidol, phenothiazines, butyrophenones, propranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone and indoramin;

22) adrenergic neurone blockers including bethanidine, debrisoquine, guabenxan, guanadrel, guanazodine, guanethidine, guanoclor and guanoxan;

23) benzodiazepines including alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam and triazolam;

24) mucolytics agents such as N-acetylcysteine, recombinant human DNase, amiloride, dextrans, heparin and low molecular weight heparin; and 25) pharmaceutically acceptable salts of any of the foregoing.

Preferably, the active agent is a small molecule, as opposed to a macromolecule. Preferably, the active agent is not a protein, and more preferably, the active agent is not insulin. In the case of proteins and in particular insulin, there is little or no benefit to be derived from the use of a force control agent in a dry powder formulation for administration by inhalation. The reason for this is that in the case of these active agents, the active agent itself acts as a force control agent and the cohesive forces of particles of these active agents are already only weak.

In preferred embodiments of the present invention, the active agent is heparin (fractionated and unfractionated), apomorphine, clobozam, clomipramine or glycopyrrolate.

The terms "additive particles" and "particles of additive material" are used interchangeably herein. The additive particles comprise one or more additive materials (or FCAs). Preferably, the additive particles consist essentially of the additive material.

Known additive materials usually consist of physiologically acceptable material, although the additive material may not always reach the lung. For example, where the additive particles are attached to the surface of carrier particles, they will generally be deposited, along with those carrier particles, at the back of the throat of the user.

Advantageously, the additive material includes one or more compounds selected from amino acids and derivatives thereof, and peptides and derivatives thereof. Amino acids, peptides and derivatives of peptides are physiologically acceptable and give acceptable release of the active particles on inhalation.

It is particularly advantageous for the additive material to comprise an amino acid. The additive material may comprise one or more of any of the following amino acids: leucine, isoleucine, lysine, valine, methionine, and phenylalanine. The additive may be a salt or a derivative of an amino acid, for example aspartame or acesulfame K. Preferably, the additive particles consist substantially of an amino acid, more preferably of leucine, advantageously L-leucine. The D- and DL-forms may also be used. As indicated above, leucine has been found to give particularly efficient dispersal of the active particles on inhalation.

The additive material may include one or more water soluble substances. This helps absorption of the additive material by the body if it reaches the lower lung. The additive material may include dipolar ions, which may be zwitterions. It is also advantageous to include a spreading agent as an additive material, to assist with the dispersal of the composition in the lungs. Suitable spreading agents include surfactants such as known lung surfactants (e.g. ALEC, Registered Trade Mark), which comprise phospholipids, for example, mixtures of DPPC (dipalmitoyl phosphatidylcholine) and PG (phosphatidylglycerol).

The phospholipids used in accordance with the invention may have acyl substituents on the phosphatidyl groups. As in their natural counterparts, the acyl groups may comprise identical or different, saturated or unsaturated acyl radicals, generally C14-22, especially C16-20, acyl radicals. Thus, the phospholipids may comprise, by way of acyl radicals, the saturated radicals palmitoyl C16:0 and stearoyl C18:0 and/or the unsaturated radicals oleoyls C18:1 and C18:2. Diacyl substitution is preferred and the phospholipids used in the compositions in accordance with the invention more particularly comprise two identical saturated acyl radicals, especially dipalmitoyl and distearoyl or a mixture of phospholipids in which such radicals predominate, in particular mixtures in which dipalmitoyl is the major diacy component. Thus, phosphatidyl choline (PC) and PG may be used may be used with the same diacylphosphatidyl profile as in PC and PG extracted from human or animal or vegetable sources, but if synthetic sources are used the dipalmitoyl component may predominate, as in the DPPC mentioned above.

Suitable surfactants include, for example, dipalmitoyl phosphatidylethanolamine (DPPE), dipalmitoyl phosphatidylinositol (DPPI). Further exemplary phospholipids include 1-palmitoyl-2-oleoyl-SN-glycero-3-phosphoglycerol (POPG), phosphoglycerides such as disteroylphosphatidylcholine, diarachidoylphosphatidylcholine dibehenoylphosphatidylcholine, diphosphatidylglycerol, short-chain phosphatidylcholines, long-chain saturated phosphatidylethanolamines, long-chain saturated phosphatidylserines, long-chain saturated phosphatidylglycerols, long-chain saturated phosphatidylinositols.

The additive material may comprise a phospholipid or a derivative thereof. Lecithin has been found to be a good material for the additive material.

The additive material may comprise a metal stearate, or a derivative thereof, for example, sodium stearyl fumarate or sodium stearyl lactylate. Advantageously, the additive material comprises a metal stearate. For example, zinc stearate, magnesium stearate, calcium stearate, sodium stearate or lithium stearate. Preferably, the additive material comprises magnesium stearate.

The additive material may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are: phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the additive may be cholesterol.

Other possible additive materials include sodium benzoate, hydrogenated oils which are solid at room temperature, talc, titanium dioxide, aluminium dioxide, silicon dioxide and starch.

In one embodiment of the invention, the additive material comprises an amino acid, a metal stearate or a phospholipid. Preferably, the additive material comprises one or more of L-, D- or DL-forms of leucine, isoleucine, lysine, valine, methionine, phenylalanine, or Aerocine, lecithin or magnesium stearate. In another embodiment, the additive material comprises leucine and preferably l-leucine.

In general, the optimum amount of additive material to be included in a dry powder formulation will depend on the chemical composition and other properties of the additive material and of the active material, as well as upon the nature of other particles, such as carrier particles, if present. In general, the efficacy of the additive material is measured in terms of the FPF of the composition.

In one embodiment of the present invention, composite active particles produced by co-jet milling according to the present invention are mixed with carrier particles made of an inert excipient material.

Where the powder composition comprises an active material, additive material and excipient material, this is referred to as a 3-component system. In contrast, a 2-component system comprises just active and additive materials.

Excipient materials may be included in powders for administration by pulmonary inhalation for a number of reasons. On the one hand, the inclusion of particles of excipient material of an appropriate size can enhance the flow properties of the powder and can enhance the powder's handleability. Excipient material is also added to powder formulations as a diluent. It can be very difficult to accurately and reproducibly administer a very small amount of powder. Where low doses of drug are required, this can pose a problem and so it can be desirable to add a diluent to the powder, to increase the amount of powder to be dispensed.

In one embodiment of the present invention, the excipient material is in the form of relatively large or coarse carrier particles. Advantageously, substantially all (by weight) of the carrier particles have a diameter which lies between about 20 µm and about 1000 µm, more preferably about 50 µm and about 1000 pm. Preferably, the diameter of substantially all (by weight) of the carrier particles is less than about 355 µm and lies between about 20 µm and about 250 µm.

Preferably at least about 90% by weight of the carrier particles have a diameter between from about 40 µm to about 180 µm. The relatively large diameter of the carrier particles improves the opportunity for other, smaller particles to become attached to the surfaces of the carrier particles and provides good flow and entrainment characteristics and improved release of the active particles in the airways to increase deposition of the active particles in the lung.

Conventional thinking regarding carrier particles is that they improve the poor flowability of formulations comprising fine particles of less than 10 µm. The poor flowability is due to the agglomeration of the fine particles which occurs due to the strong attractive forces between the small particles. In the presence of large carrier particles, these attractive forces cause the fine particles to become attached to the surface of the large carrier particles, forming (usually discontinuous) coatings. This arrangement of the large and fine particles leads to better flow characteristics than is observed with a formulation made up solely of fine active particles.

The carrier particles to be added to the composite active particles of the present invention are relatively large particles of an excipient material, such as lactose.

The ratios in which the carrier particles and composite active particles are mixed will, of course, depend on the type of inhaler device used, the type of active particles used and the required dose. The carrier particles may be present in an amount of at least about 50%, more preferably at least about 70%, more preferably at least about 80%, advantageously at least about 90% and most preferably at least about 95%, based on the combined weight of the composite active particles and the carrier particles.

A 3-component system including carrier particles, such as the one described above, would be expected to work well in a passive device. The presence of the carrier particles makes the powder easier to extract from the blister, capsule or other storage means. The powder extraction tends to pose more of a problem in passive devices, as they do not create as turbulent an air flow through the blister upon actuation as active devices. This means that it can be difficult to entrain all of the powder in the air flow. The powder entrainment in a passive device is made easier where the powder includes carrier particles as this will mean that the powder is less cohesive and exhibits better flowability, compared with a powder consisting entirely of smaller particles, for example all having a diameter of less than 10 µm.

Where carrier particles and the composite active particles made according to the present invention are mixed, the active particles should readily release from the surface of the carrier particles upon actuation of the dispensing device by virtue of the additive material on the surface of the active particles. This release may be further improved where the carrier particles also have additive material applied to their surfaces. This application can be achieved by simple gentle blending or co-milling, for example as described in WO 97/03649.

However, the combination of large carrier particles and fine active particles has its disadvantages. It can only be effectively used with a relatively low (usually only up to 5%) drug content. As greater proportions of fine particles are used, more and more of the fine particles fail to become attached to the large carrier particles and segregation of the powder formulation becomes a problem. This, in turn, can lead to unpredictable and inconsistent dosing. The powder also becomes more cohesive and difficult to handle.

Furthermore, the size of the carrier particles used in a dry powder formulation can be influential on segregation.

Segregation can be a catastrophic problem in powder handling during manufacture and the filling of devices or device components (such as capsules or blisters) from which the powder is to be dispensed. Segregation tends to occur where ordered mixes cannot be made sufficiently stable. Ordered mixes occur where there is a significant disparity in powder particle size. Ordered mixes become unstable and prone to segregation when the relative level of the fine component increases beyond the quantity which can adhere to the larger component surface, and so becomes loose and tends to separate from the main blend. When this happens, the instability is actually exacerbated by the addition of anti-adherents/glidants such as FCAs.

In the case of dry powder formulations of micron-sized drug, and typical 60 to 150 µm sized carrier, this instability tends to occur once drug content exceeds a few percent, the exact amount is dependent on the drug. However, it has been found that a carrier with a particle size of <30 µm tends not to exhibit this instability. This is thought to be due to the fine carrier particles having relatively higher surface area compared to the coarse carrier particles, and the similarity between the size of the active particles and the carrier particles. Such fine carrier particles are not often used, mainly because of their poor flow characteristics, as discussed above.

According to another embodiment of the present invention, the 3-component system comprises the composite active particles made according to the present invention, together with fine excipient particles. Such excipient particles have a particle size of 30 µm or less, preferably 20 µm or less and more preferably 10 i.im or less. The excipient particles advantageously have a particle size of 30 to 5 μm.

One would expect such a powder formulation, made up of only fine particles with a particle size of less than 10 μm, to suffer from the cohesion and flowability problems observed with formulations comprising just fine active particles. The active particles do not coat the fine excipient particles, as they do the large carrier particles, because of the different forces existing between fine particles and fine and large particles.

However, where the powder formulation comprises composite active particles according to the present invention and fine excipient particles, it has been surprisingly found that such formulations are efficiently dispensed by an active device. It has been found that the potentially poor flow characteristics or—handleability of powders comprising only particles with a size of less than 10 μm are not significant when the powder is dispensed using an active inhaler device.

As mentioned above, the active device causes turbulence within the blister, capsule or other powder storage means. This means that even powders with fine excipient particles can be extracted. Furthermore, the presence of the composite active particles means that the agglomerates formed from the fine particles are not so stable that they are not broken up upon actuation of the inhaler device. Thus, it has been surprisingly found that compositions comprising the composite active particles of the present invention and fine particles of an inert excipient material, such as lactose, can be efficiently dispensed using an active inhaler device.

In another embodiment of the present invention, the fine excipient particles added to the composite active particles are themselves co-jet milled with additive material. The co-jet milling of the active particles with additive material and of the excipient particles with additive material can occur separately or together, and by similar or different forms of co-milling. For example, the active particles may be co-jet milled, the excipient particles may be co-processed by a compressive form of milling such as mechanofusion or similar processes, or visa versa. The quantities and nature of additives may be different for active and excipient. This may be the case where the two groups of particles have different sizes and hence relative surface areas.

Co-jet milling the fine excipient particles with the additive material results in coating of the additive material on the surfaces of the excipient particles. This coating can further reduce the cohesiveness of the 3-component system and can further enhance deagglomeration upon actuation of the inhaler device.

Generally, flow of compositions comprising fine carrier particles is poor unless they are pelletised (e.g. as is done in the AstraZeneca product OXIS (registered trade mark). However, using the processes of the present invention, fine lactoses (e.g. Sorbolac 400 with a particle size of 1 to 15 pm) have been produced which flow sufficiently well for use in DPIs with >5% drug, and up to approximately 30% and possibly 50% cohesive micronised drug. It should be noted that these beneficial properties are achieved without the need to resort to pelletisation, which has its own disadvantages of being difficult to do and generally decreasing FPFs.

Thus, the co-milling of the fine excipient particles and additive material in accordance with the present invention allows one to produce blends of active and excipient materials with a much greater range of active agent content than is possible using conventional carrier particles (i.e. >5%). The resultant dry powder formulations also benefit from improved aerosolisation.

In the present invention, different grinding and injection pressures may be used in order to produce particles with different coating characteristics. The invention also includes embodiments where different grinding and injection pressures are combined, to produce composite particles with desired properties, that is, to engineer the particles.

Co-jet milling may be carried out at grinding pressures between 0.1 and 12 bar. Varying the pressure allows one to control the degree of particle size reduction. At pressures in the region of 0.1-3 bar, more preferably 0.5-2 bar and most preferably 1-2 bar, the co-jet milling will primarily result in blending of the active and additive particles, so that the additive material coats the active particles. On the other hand, at 3-12 bar, and preferably 5-12 bar, the co-jet milling will additionally lead to particle size reduction.

In one embodiment, the jet milling is carried out at a grinding pressure of between 0.1 and 3 bar, to achieve blending of the active and additive particles. As discussed below in greater detail, when the co-jet milling of the present invention is carried out at such relatively low pressures, the resultant particles have been shown to perform well when dispensed using passive devices. It is speculated that this is because the particles are larger than those produced by co-jet milling at higher pressures and these relatively larger particles are more easily extracted from the blister, capsule or other storage means in the passive device, due to less cohesion and better flowability. Whilst such relatively large particles are easily extracted from the blister or capsule in an active device, they may result in throat deposition.

In another embodiment, the jet milling is carried out at a grinding pressure of between 3 and 12 bar, to achieve a reduction of the sizes of the active and additive particles. The co-jet milling at these relatively high pressures can produce extremely small composite active particles having an MMAD of between 3 and 0.5 pm. These fine particle sizes are excellent for deep lung deposition, but they really need to be dispensed using an active inhaler device, as the powder formulations comprising such fine particles are actually rather "sticky". As discussed below, this stickiness may not pose a problem for active devices and is actually thought to be advantageous as it can slow the extraction of the powder so that the composite active particles travel more slowly in the powder plume generated by the device, thereby reducing throat deposition.

Tests were carried out whereby pre-micronised lactose (as a drug model) was co-jet milled in an MC50 Hosakawa Micron with 5% magnesium stearate. At 2 bar milling pressure, the resultant material had a d(50) of approximately 3 μm, whilst milling the same mixture at around 7 bar resulted in material with a d(50) of about 1 μm. Thus, when operating with a jet milling pressure of 0.1-3 bar little milling, that it is particle size reduction, is seen. From 3-12 bar milling pressure, increasing milling is seen, with the particle size reduction increasing with the increasing pressure. This means that the milling pressure may be selected according to the desired particle size in the resultant mixture. In one embodiment, the step of jet milling is carried out at an inlet pressure between 0.1 and 3 bar. Alternatively, the step of jet milling is carried out at an inlet pressure of between 3 and 12 bar.

As indicated above, co-jet milling at lower pressures produces powders which perform well in passive devices whilst powders milled at higher pressures perform better in active devices, such as Aspirair (trade mark).

The co-jet milling processes according to the present invention can also be carried out in two or more stages, to combine the beneficial effects of the milling at different pressures and/or different types of milling or blending processes. The use of multiple steps allows one to tailor the properties of the co-jet milled particles to suit a particular inhaler device, a particular drug and/or to target particular parts of the lung.

In one embodiment, the milling process is a two-step process comprising first jet-milling the drug on its own at high grinding pressure to obtain the very small particle sizes possible using this type of milling. Next, the milled drug is co-jet milled with an additive material. Preferably, this second step is carried out at a lower grinding pressure, so that the effect is the coating of the small active particles with the additive material.

The additive material may also be milled on its own prior to the co-milling step. This milling may be conducted in a jet mill, a ball mill, a high pressure homogeniser or alternative known ultrafine milling methods. The particles of additive material are preferably in a form with 90% of the particles by mass of diameter <10 µm, more preferably <5 µm, more preferably <2 µm, more preferably <1 µm and most preferably <0.5 µm.

This two-step process produces better results than simply co-jet milling the active material and additive material at a high grinding pressure. Experimental results discussed below show that the two-step process results in smaller particles and less throat deposition than simple co-jet milling of the materials at a high grinding pressure.

In another embodiment of the present invention, the particles produced using the two-step process discussed above subsequently undergo mechanofusion or an equivalent compressive process. This final mechanofusion step is thought to "polish" the composite active particles, further rubbing the additive material into the particles. This allows one to enjoy the beneficial properties afforded to particles by mechanofusion, in combination with the very small particles sizes made possible by the co-jet milling.

The reduction in particle size may be increased by carrying out the co-jet milling at lower temperatures. Whilst the co-jet milling process may be carried out at temperatures between −20° C. and 40° C., the particles will tend to be more brittle at lower temperatures, and they therefore fracture more readily so that the milled particles tend to be even smaller. Therefore, in another embodiment, the jet milling is carried out at temperatures below room temperature, preferably at a temperature below 10° C., more preferably at a temperature below 0° C.

Preferably, all of the particles are of a similar size distribution. That is, substantially all of the particles are within the size range of about 0 to about 5 µm, of about 0 to about 20 µm, of about 0 to 10 µm, of about 0 to 5 µm or of about 0 to 2 µm.

In accordance with a second aspect of the present invention, a pharmaceutical dry powder composition for pulmonary inhalation is provided, comprising composite active particles made by a method according to the first aspect of the invention.

The MMAD of the composite active particles is preferably not more than 10 µm, and advantageously it is not more than 5 µm, more preferably not more than 3 µm, even more preferably not more than 2 µm, more preferably not more than 1.8 µm more preferably not more than 1.5 µm, even more preferably not more than 1.2 µm and most preferably not more than 1 µm.

Accordingly, advantageously at least 90% by weight of the composite active particles have a diameter of not more than 10 µm, advantageously not more than 5 µm, preferably not more than 3 µm, even more preferably not more than 2.5 µm, even more preferably not more than 2 µm and more preferably not more than 1.5 µm, or even not more than 1.0 µm.

It is an aim of the present invention to optimise the powder properties, so that the FPF and FPD are improved compared to those obtained using known powder formulations, regardless of the type of device used to dispense the composition of the invention.

It is a particular aim of the present invention to provide a dry powder formulation which has an FPF of at least 40%. Preferably, the FPF(ED) will be between 60 and 99%, more preferably between 70 and 99%, more preferably between 80 and 99% and even more preferably between 90 and 99%. Furthermore, it is desirable for the FPF(MD) to be at least 40%. Preferably, the FPF(MD) will be between 40 and 99%, more preferably between 50 and 99%, more preferably between 60 and 99%, and more preferably between 70 and 99% and even more preferably between 80 and 99%.

In a preferred embodiment of the present invention the resultant dry powder formulation has a reproducible FPF (ED) of at least 70%. Preferably, the FPF(ED) will be at least 80%, more preferably the FPF(ED) will be at least 85%, and most preferably the FPF(ED) will be at least 90%.

In a further preferred embodiment, the dry powder formulation has a reproducible FPF(MD) of at least 60%. Preferably, the FPF(MD) will be at least 70%, more preferably the FPF(MD) will be at least 80%, and most preferably the FPF(MD) will be at least 85%.

As illustrated by the experimental results set out below, it has been surprisingly found that co-milling active particles with additive particles using jet milling results in composite active particles having significantly better FPF and FPD than those produced by co-milling using mechanofusion, when the powders are dispensed using the active inhaler device Aspirair (trade mark).

This unexpected improvement in the FPF and FPD of the powder formulations prepared is thought to be due to the following factors. Firstly, the milling process results in very small particles. Secondly, there appears to be only partial coverage of the particles with the force control agent and this means that some of the particle cohesion is retained, affording better powder handleability despite the very small particle sizes.

Co-jet milling has surprisingly been found to be capable of significantly reducing the median primary particle size of active particles (for example, from 3 or 2 µm to 1 µm), while also allowing good aerosolisation from a delivery device. This further reduction in primary particle size is considered to be advantageous for delivery of systemically targeted molecules to the deep lung. The benefit here is to co-jet mill active particles with additive particles in order to reduce primary particle size while still achieving a reduction in the level of powder cohesion and adhesion by coating the particles for additive material.

Test Methods

All materials were evaluated in the Next Generation Impactor (NGI). Details of the test are provided in each case.

Formulations were processed using:

1) The Hosokawa Micron MechanoFusion AMS Mini system. This system was operated with a novel rotor, providing a 1 mm compression gap; and 2) The Hosokawa Micron AS50 spiral jet mill.

The in-vitro testing was performed using an Aspirair (trade mark) device, which is an active inhaler device.

The formulations were composed of one or more of the following constituents:

Magnesium stearate (standard grade)
L-Leucine (Ajinomoto) and jet milled by Micron Technologies
Sorbolac 400 lactose
Micronised clobozam
Micronised apomorphine hydrochloride
Micronised lactose
Re-condensed Leucine (Aerocine)

Comparison of Co-Jet Milled and Mechanofused Formulations (Clobozam)

The following is a comparison of 2-component systems comprising co-jet milled or mechanofused active particles and additive material.

1.01 g of micronised clobozam was weighed out, and then gently pressed through a 300 μm metal sieve, using the rounded face of a metal spatula. This formulation was recorded as "3A".

9.37 g of micronised clobozam was then combined with 0.50 g of micronised L-leucine in the MechanoFusion system. The material was processed at a setting of 20% power for 5 minutes, followed by a setting of 80% power for 10 minutes. This material was recorded as "4A". After blending, this powder was then gently pushed through a 300 μm metal sieve with a spatula. This material was recorded as "4B".

9.57 g of micronised clobozam was then combined with 0.50 g of magnesium stearate in the MechanoFusion system. The material was processed at a setting of 20% power for 5 minutes, followed by a setting of 80% power for 10 minutes. This material was recorded as "5A". After blending, this powder was rested overnight, and then was gently pushed through a 300 μm metal sieve with a spatula. This material was recorded as "5B".

9.5 g of micronised clobozam was then combined with 0.50 g of micronised L-leucine in the MechanoFusion system. The material was processed at a relatively low speed setting of 20% power for 5 minutes. This process was intended only to produce a good mix of the components. This material was recorded as "6A".

6.09 g of "6A" fed at approximately 1 g per minute into an AS50 spiral jet mill, set with an injector pressure of about 7 bar and a grinding pressure of about 5 bar. The resulting material was recovered and recorded as "6B".

After milling, this powder was rested overnight, and then was gently pushed through a 300 μm metal sieve with a spatula. This material was recorded as "6C".

9.5 g of micronised clobozam was then combined with 0.50 g of magnesium stearate in the MechanoFusion system. The material was processed at a setting of 20% power for 5 minutes. This material was recorded as "7A".

6.00 g of "7A" was fed at approximately 1 g per minute into the AS50 spiral jet mill, set with an injector pressure of about 7 bar and a grinding pressure of about 5 bar. The resulting material was recovered and recorded as "7B".

After milling, this powder was gently pushed through a 300 μm metal sieve with a spatula. This material was recorded as "7C".

A batch of re-condensed leucine (also referred to as "Aerocine") was produced by subliming to vapour a sample of leucine in a tube furnace, and re-condensing as a very finely dispersed powder as the vapour cooled. This batch was identified as "8A".

9.5 g of micronised clobozam was then combined with 0.50 g of Aerocine, in the MechanoFusion system. The material was processed at a setting of 20% power for 5 minutes, followed by a setting of 80% power for 10 minutes. This material was recorded as "8B". After blending, this powder was rested overnight, and then was gently pushed through a 300 μm metal sieve with a spatula. This material was recorded as "8C".

9.5 g of micronised clobozam was combined with 0.50 g of Aerocine in the MechanoFusion system. The material was processed at a setting of 20% power for 5 minutes. 7.00 g of this powder was then fed into the AS50 spiral jet mill, set with an injector pressure of about 7 bar and a grinding pressure of about 5 bar. The resulting material was recovered and recorded as "9A".

After milling, this powder was gently pushed through a 300 μm metal sieve with a spatula. This material was recorded as "9B".

A number of foil blisters were filled with approximately 2 mg of the following clobozam formulations:

3A—no milling & no additive material

4B—leucine & mechanofused

5B—magnesium stearate & mechanofused

6C—leucine & co-jet milled

7C—magnesium stearate & co-jet milled

8C—Aerocine & co-jet milled

9B—Aerocine & mechanofused.

These formulations were then fired from an Aspirair device into an NGI at a flow rate of 60 l/m. The Aspirair was operated under 2 conditions for each formulation: with a reservoir of 15 ml of air at 1.5 bar or with a reservoir of 30 ml of air at 0.5 bar.

Full details of the results are attached. The impactor test results are summarised in Tables 1, 2 and 3 below.

TABLE 1

| Formulation | MD (mg) | ED (mg) | FPD(mg) (<5 μm) | MMAD |
|---|---|---|---|---|
| 3A 0.5 bar 30 ml | 2.04 | 1.12 | 0.88 | 2.91 |
| 3A 1.5 bar 15 ml | 1.92 | 1.74 | 1.23 | 2.86 |
| 4B 0.5 bar 30 ml | 1.84 | 1.48 | 0.82 | 3.84 |
| 4B 1.5 bar 15 ml | 1.80 | 1.56 | 0.81 | 3.32 |
| 5B 0.5 bar 30 ml | 1.84 | 1.53 | 1.17 | 2.34 |
| 5B 1.5 bar 15 ml | 1.85 | 1.55 | 1.12 | 2.22 |
| 6C 0.5 bar 30 ml | 1.93 | 1.80 | 1.67 | 2.11 |
| 6C 1.5 bar 15 ml | 1.86 | 1.73 | 1.62 | 2.11 |
| 6C 1.5 bar 15 ml (silicon coated plates) | 1.97 | 1.86 | 1.67 | 2.07 |
| | 1.74 | 1.65 | 1.46 | 2.03 |
| 7C 0.5 bar 30 ml | 2.06 | 1.99 | 1.87 | 1.97 |
| 7C 1.5 bar 15 ml | 1.89 | 1.78 | 1.63 | 1.79 |
| 8C 0.5 bar 30 ml | 1.82 | 1.73 | 1.62 | 2.02 |
| 8C 1.5 bar 15 ml | 1.81 | 1.74 | 1.57 | 2.01 |
| 9B 0.5 bar 30 ml | 1.88 | 1.73 | 1.04 | 3.48 |
| 9B 1.5 bar 15 ml | 1.80 | 1.64 | 0.94 | 3.12 |

TABLE 2

| Formulation | FPF(MD) % (<5 μm) | FPF(ED) % (<5 μm) | FPF(ED) % (<3 μm) | FPF(ED) % (<2 μm) | FPF(ED) % (<1 μm) |
|---|---|---|---|---|---|
| 3A 0.5 bar 30 ml | 43 | 78 | 49 | 32 | 17 |
| 3A 1.5 bar 15 ml | 64 | 71 | 45 | 24 | 6 |
| 4B 0.5 bar 30 ml | 45 | 55 | 28 | 15 | 7 |
| 4B 1.5 bar 15 ml | 45 | 52 | 30 | 18 | 9 |
| 5B 0.5 bar 30 ml | 64 | 77 | 54 | 42 | 30 |
| 5B 1.5 bar 15 ml | 61 | 72 | 52 | 38 | 25 |
| 6C 0.5 bar 30 ml | 87 | 93 | 77 | 44 | 8 |
| 6C 1.5 bar 15 ml | 87 | 94 | 76 | 44 | 9 |
| 6C 1.5 bar 15 ml | 85 | 90 | 73 | 44 | 10 |
| 6C 1.5 bar 15 ml (silicon coated plates) | 84 | 89 | 74 | 45 | 8 |
| 7C 0.5 bar 30 ml | 91 | 94 | 79 | 50 | 14 |
| 7C 1.5 bar 15 ml | 86 | 92 | 82 | 56 | 16 |
| 8C 0.5 bar 30 ml | 89 | 93 | 79 | 48 | 12 |
| 8C 1.5 bar 15 ml | 87 | 90 | 76 | 46 | 9 |
| 9B 0.5 bar 30 ml | 55 | 60 | 34 | 24 | 15 |
| 9B 1.5 bar 15 ml | 52 | 57 | 34 | 24 | 15 |

TABLE 3

| Formulation | *recovery | *throat | *blister | *device |
|---|---|---|---|---|
| 3A 0.5 bar 30 ml | 102% | 3% | 1% | 43% |
| 3A 1.5 bar 15 ml | 96% | 15% | 1% | 8% |
| 4B 0.5 bar 30 ml | 97% | 15% | 7% | 12% |
| 4B 1.5 bar 15 ml | 95% | 27% | 6% | 8% |
| 5B 0.5 bar 30 ml | 97% | 7% | 13% | 4% |
| 5B 1.5 bar 15 ml | 98% | 14% | 12% | 4% |
| 6C 0.5 bar 30 ml | 97% | 2% | 1% | 6% |
| 6C 1.5 bar 15 ml | 101% | 3% | 1% | 5% |
| 6C 1.5 bar 15 ml | 104% | 6% | 3% | 3% |
| 6C 1.5 bar 15 ml (silicon coated plates) | 91% | 8% | 1% | 4% |
| 7C 0.5 bar 30 ml | 110% | 2% | 1% | 3% |
| 7C 1.5 bar 15 ml | 99% | 6% | 2% | 3% |
| 8C 0.5 bar 30 ml | 99% | 3% | 1% | 4% |
| 8C 1.5 bar 15 ml | 95% | 6% | 1% | 3% |
| 9B 0.5 bar 30 ml | 96% | 16% | 2% | 7% |
| 9B 1.5 bar 15 ml | 95% | 26% | 4% | 5% |

From these results it can be seen that the co-jet milled formulations exhibited exceptional FPFs when dispensed from an active dry powder inhaler device. The FPFs observed were significantly better that those of the mechanofused formulations and those formulations which did not include an additive material. This improvement would appear to be largely due to reduced throat deposition, which was less than 8% for the co-jet milled formulations, compared to 15% for the pure drug and up to 27% for the mechanofused formulations.

The reproducibility of the FPFs obtained was also tested. Through life dose uniformity for the primary candidate, 6C, the preparation of which is described above, was tested by firing 30 doses, with the emitted doses collected by DUSA. Through life dose uniformity results are presented in the graph of FIG. 8.

The mean ED was 1965 μg, with an RSD (relative standard deviation) of 2.8%. This material consequently demonstrated excellent through life dose reproducibility.

The particle size distributions of these powdered materials indicate both the level of size reduction obtained by the co-milling, and the level of dispersion efficiency at varied pressures. The d(50) and d(97) plots provide a further indication of this dispersibility of the powders as a function of pressure.

Formulation 5B exhibited much the best dispersion.

This set of dispersibility tests shows that the MechanoFused powders disperse more easily at lower pressures than the original drug, and that magnesium stearate gives the best dispersion within these, followed by Aerocine and leucine. The co-jet milled powders do not appear to disperse any more easily in this test than the original drug, however the primary particle sizes (d(50)) are reduced.

Comparison of Co-Jet Milled and Mechanofused Formulations (Apomorphine)

In order to establish the effect of co-jet milling on different active agents, apomorphine hydrochloride formulations with fine carrier particles (i.e. a 3-component system) were prepared and tested.

19.0 g of Sorbolac 400 lactose and 1.0 g of micronised L-leucine were combined in the MechanoFusion system. The material was processed at a setting of 20% power for 5 minutes, followed by a setting of 80% power for 10 minutes. This material was recovered and recorded as “2A”.

15.0 g of apomorphine hydrochloride and 0.75 g of micronised L-leucine were combined in the MechanoFusion system. The material was processed at a setting of 20% power for 5 minutes, followed by a setting of 80% power for 10 minutes. This material was recovered and recorded as “2B”.

2.1 g “2B’ plus 0.4 g micronised leucine were blended by hand in a mortar and pestle for 2 minutes. 2.5 g micronised lactose was added and blended for a further 2 minutes. 5 g micronised lactose was added and blended for another 2 minutes. This mixture was then processed in the AS50 Spiral jet mill using an inlet pressure of 7 bar and a grinding pressure of 5 bar, feed rate 5 ml/min. This powder was gently pushed through a 3001 .im metal sieve with a spatula. This material was recorded as “10A”.

1.5 g “10A” was combined with 0.20 g micronised L-leucine and 3.75 g of Sorbolac 400 lactose by hand in a mortar with a spatula for 10 minutes. This powder was gently pushed through a 300 μm metal sieve with a spatula. This material was recorded as “10B”.

9 g micronised apomorphine HCl plus 1 g micronised leucine were placed in the MechanoFusion system and processed at 20% (1000 rpm) for 5 minutes. This initial blend was then processed in the AS50 Spiral jet mill using an inlet pressure of 7 bar and a grinding pressure of 5 bar, feed rate 5 ml/min This material was recorded as “11A”.

After blending, this powder was rested overnight, and then was gently passed through a 300 μm metal sieve by shaking. This material was recorded as "11B".

2 g micronised apomorphine HCl plus 0.5 g micronised leucine were blended by hand in mortar and pestle for 2 minutes. 2.5 g micronised lactose was added and blended for a further 2 minutes. Then 5 g micronised lactose was added and blended for another 2 minutes. This mixture was then processed in the AS50 Spiral jet mill using an inlet pressure of 7 bar and a grinding pressure of 5 bar, feed rate 5 ml/min. This powder was gently pushed through a 300 μm metal sieve with a spatula. This material was recorded as "12A".

16.5 g of Sorbolac 400 and 0.85 g of micronised leucine were placed in the MechanoFusion system and processed at 20% (1000 rpm) for 5 minutes then at 80% (4000 rpm) for 10 minutes. This material was recorded as "13A".

0.5 g micronised apomorphine HCl plus 2.0 g "13A" were blended by hand in a mortar with a spatula for 10 minutes. This powder was gently pushed through a 300 μm metal sieve with a spatula. This material was recorded as "13B".

A number of foil blisters were filled with approximately 2 mg of the following formulations:

10A—20% apomorphine HCl, 5% 1-leucine, 75% micronised lactose (co-jet milled)

10C—26.2% apomorphine HCl, 5% 1-leucine, 68.7% sorbolac (geometric)

11B—95% apomorphine HCl, 5% 1-leucine (co-jet milled)

12A—20% apomorphine HCl, 5% leucine, 75% micronised lactose (all co-jet milled)

13B—20% apomorphine HCl, 5% 1-leucine, 75% Sorbolac 400 (leucine & Sorbolac mechanofused)

These were then fired from an Aspirair device into an NGI at a flow rate of 601/m. The Aspirair was operated with a reservoir of 15 ml at 1.5 bar. Each in vitro test was conducted once to screen, and then the selected candidates were repeated. Further candidates were also repeated in ACI at 601/m.

TABLE 4

| Formulation | MD (μg) | ED (μg) | FPD (μg) (<5 μm) | MMAD |
|---|---|---|---|---|
| 10A | 384 | 356 | 329 | 1.78 |
| 13B | 359 | 327 | 200 | 1.54 |
| | (1793) | (1635) | (1000) | |
| 10C | 523 | 492 | 374 | 1.63 |
| 11B | 1891 | 1680 | 1614 | 1.36 |
| | 1882 | 1622 | 1551 | 1.44 |
| | 1941 | 1669 | 1601 | 1.49 |
| Ave. | 1905 | 1657 | 1589 | 1.43 |
| SD | 32 | 31 | 33 | 0.07 |
| RSD | 1.7 | 1.9 | 2.1 | 4.6 |
| 11B | 1895 | 1559 | 1514 | 1.58 |
| | 1895 | 1549 | 1485 | 1.62 |
| | 1923 | 1565 | 1504 | 1.62 |
| ACI | | | | |
| Ave. | 1904 | 1558 | 1501 | 1.61 |
| SD | 16 | 8 | 15 | 0.02 |
| RSD | 1 | 1 | 1 | 1 |
| 12A | 414 | 387 | 363 | 1.63 |
| | 410 | 387 | 363 | 1.66 |
| | 406 | 378 | 355 | 1.68 |

TABLE 4-continued

| Formulation | MD (μg) | ED (μg) | FPD (μg) (<5 μm) | MMAD |
|---|---|---|---|---|
| Ave. | 410 | 384 | 360 | 1.66 |
| SD | 4 | 5 | 5 | 0.03 |
| RSD | 1 | 1 | 1 | 2 |
| Total ave. | 2050 | 1920 | 1800 | |
| 12A | 395 | 365 | 341 | 1.80 |
| | 411 | 385 | 360 | 1.85 |
| | 400 | 370 | 349 | 1.84 |
| ACI | | | | |
| Ave. | 402 | 373 | 350 | 1.83 |
| SD | 8 | 10 | 10 | 0.04 |
| RSD | 2 | 3 | 3 | 2 |
| Total ave. | 2011 | 1866 | 1750 | |

TABLE 5

| Formulation 2 mg, 1.5 bar 15 ml reservoir 601/min | FPF(MD) % (<5 μm) | FPF(ED) % (<5 μm) | FPF(ED) % (<3 μm) | FPF(ED) % (<2 μm) | FPF(ED) % (<1 μm) |
|---|---|---|---|---|---|
| 10A | 86 | 93 | 87 | 60 | 13 |
| 13B | 56 | 61 | 52 | 42 | 19 |
| 10C | 72 | 76 | 67 | 51 | 16 |
| 11B | 85 | 96 | 95 | 81 | 24 |
| | 82 | 96 | 93 | 77 | 22 |
| | 82 | 96 | 92 | 74 | 20 |
| Ave. | 83 | 96 | 93 | 77 | 22 |
| SD | | 0 | 1.5 | 3.5 | 2 |
| RSD | | 0 | 1.6 | 4.5 | 9.1 |
| 11B | 80 | 97 | 94 | 74 | 14 |
| | 78 | 96 | 93 | 70 | 14 |
| | 78 | 96 | 94 | 72 | 12 |
| ACI | | | | | |
| Ave. | 79 | 96 | 94 | 72 | 13 |
| SD | | 1 | 1 | 2 | 1 |
| RSD | | 1 | 1 | 3 | 9 |
| 12A | 88 | 94 | 89 | 68 | 13 |
| | 89 | 94 | 89 | 66 | 12 |
| | 87 | 94 | 88 | 64 | 12 |
| Ave. | 88 | 94 | 89 | 66 | 12 |
| SD | | 0 | 1 | 2 | 1 |
| RSD | | 0 | 1 | 3 | 5 |
| 12A | 86 | 94 | 85 | 57 | 9 |
| | 88 | 93 | 84 | 55 | 8 |
| | 87 | 94 | 85 | 56 | 8 |
| ACI | | | | | |
| Ave. | 87 | 94 | 85 | 56 | 8 |
| SD | | 1 | 1 | 1 | 1 |
| RSD | | 1 | 1 | 2 | 7 |

TABLE 6

| Formulation 2 mg, 1.5 bar 15 ml reservoir 601/min | Recovery | Throat | Blister | Device |
|---|---|---|---|---|
| 10A | 96% | 5% | 0.3% | 7% |
| 13B | 94% | 29% | 3% | 6% |
| 10C | 100% | 16% | 2% | 4% |
| 11B | 101% | 2% | 0.6% | 10% |
| | 99% | 2% | 0.2% | 14% |
| | 102% | 2% | 0.3% | 14% |
| Ave. | 101% | 2% | 0.4% | 13% |
| SD | 1.5 | 0 | 0.2 | 2.3 |

TABLE 6-continued

| Formulation 2 mg, 1.5 bar 15 ml reservoir 60 l/min | Recovery | Throat | Blister | Device |
|---|---|---|---|---|
| RSD | 1.5 | 0 | 57 | 18 |
| 11B | 100% | 1% | 0.5% | 17% |
|  | 100% | 2% | 0.1% | 18% |
|  | 101% | 2% | 0.4% | 18% |
| ACI |  |  |  |  |
| Ave. | 100% | 2% | 0.3% | 18% |
| SD | 1 | 1 | 0.2 | 1 |
| RSD | 1 | 35 | 62 | 3 |
| 12A | 109% | 4% | 0.3% | 6% |
|  | 108% | 4% | 0.2% | 6% |
|  | 107% | 4% | 0.02% | 7% |
| Ave. | 108 | 4% | 0.2 | 6% |
| SD | 1 | 0 | 0.1 | 1 |
| RSD | 1 | 0 | 82 | 9 |
| 12A | 104% | 3% | 0.4% | 7% |
|  | 108% | 4% | 0.2% | 6% |
|  | 105% | 2% | 0.4% | 7% |
| ACI |  |  |  |  |
| Ave. | 106% | 3% | 0.3 | 7% |
| SD | 2 | 1 | 0.1 | 1 |
| RSD | 2 | 33 | 35 | 9 |

The co-jet milled formulations once again exhibited exceptional FPFs when it is dispensed using an active dry powder inhaler device. The improvement appears to be largely due to reduced throat deposition which was less than 5%, compared to between 16 and 29% for the mechanofused formulations. "12A" was produced as a repeat of "10A", but excluding the mechanofused pre-blend (to show it was not required).

The reproducibility of the FPFs obtained with the formulation 12A, the preparation of which is described above, was tested.

Figure 2:
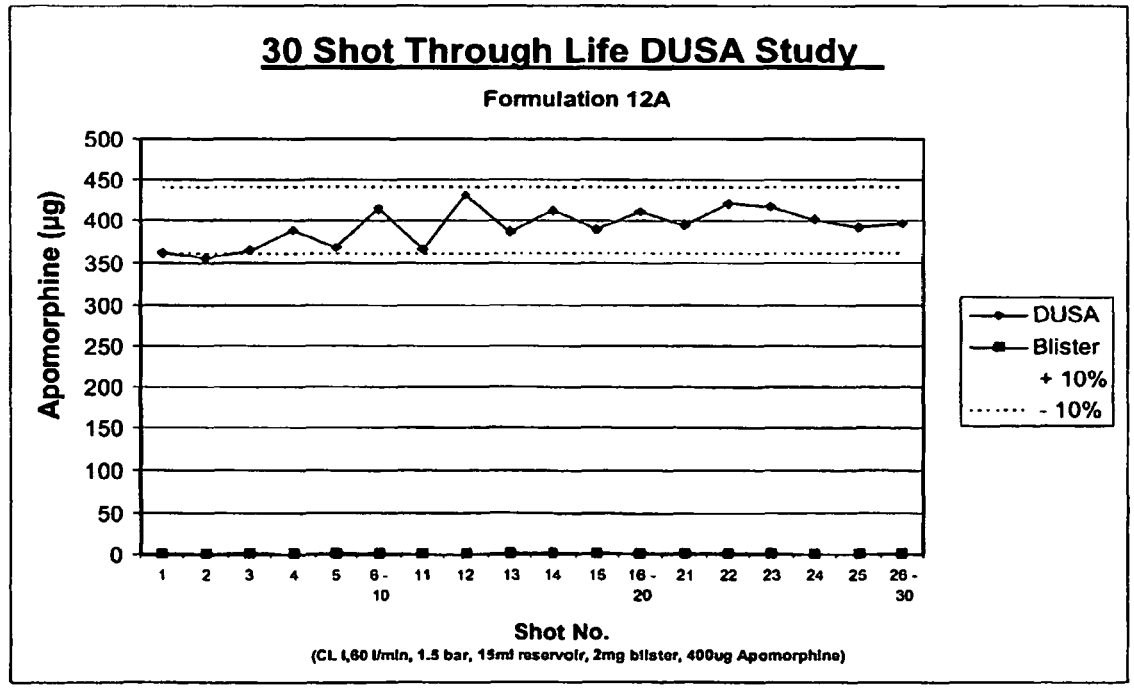
FIG. 2 is a graph presenting the life dose uniformity for formulation "12A".

A number of foil blisters were filled with approximately 2 mg of formulation 12A. Through life dose uniformity was tested by firing 30 doses, with the emitted doses collected by DUSA. Through life dose uniformity results are presented in the graph in FIG. 2.

The mean ED was 389 μg, with an RSD of 6.1% and the through life delivery of this drug-lactose formulation was very good.

In order to investigate the cause of the unexpected differences between the co-jet milled formulations and those prepared by mechanofusion, formulations "11B", "10A" and "2C" were fired from an Aspirair and plume and vortex behaviour recorded on digital video. The images were studied in light of the above differences in throat deposition.

Video of plume behaviour indicated a difference between the co-jet milled formulations and mechanofused formulations. Mechanofused formulations showed a highly concentrated fast moving bolus at the front of the air jet. Most powder appeared to have been emitted after approximately 40 ms. Co-jet milled formulations showed a greater spread of the plume. The plume front moves at a similar velocity, but the front is less concentrated, appears to slow more quickly and powder is emitted for considerably longer (i.e. >200 ms).

Video of the vortex showed that the mechanofused powders enter the vortex within 10 ms, whereas co-jet milled formulations take at least 30 ms. Similarly the mechanofused powders appeared quicker to leave the vortex, with the co-jet milled materials forming a more prolonged fogging of the vortex. The behaviour observed for co-jet milled materials was described as an increased tendency to stick, but then scour from the inside of the vortex.

Particle size distributions of the raw materials and selected formulations were determined by Malvern particle sizer, via the Scirroco dry powder disperser. The data are summarised in the graphs shown in FIGS. 3 to 10.

Figure 3:
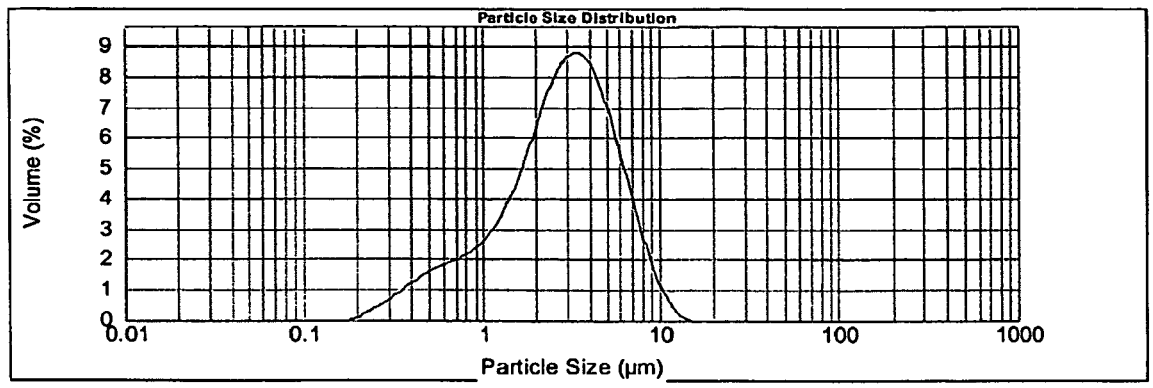
FIG. 3 shows the particle size distribution of the raw material micronized lactose.

FIG. 3 shows the particle size distribution of the raw material micronised lactose.

Figure 4:
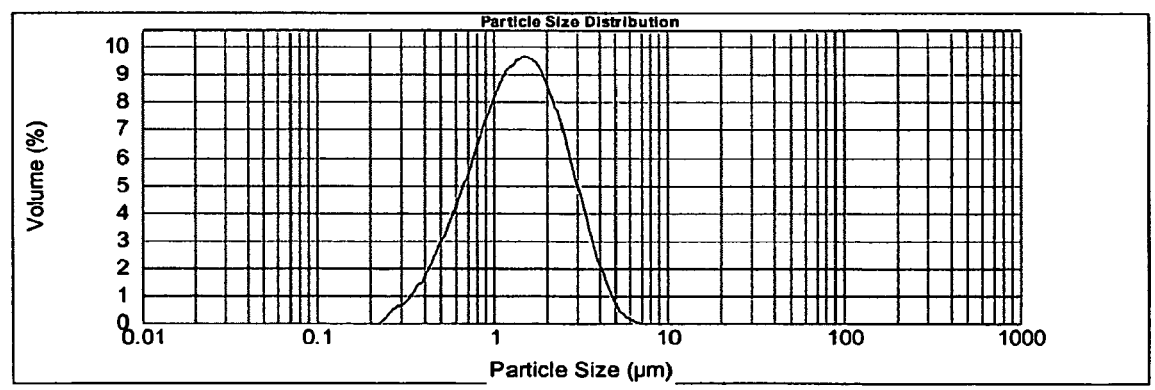
FIG. 4 shows the particle size distribution of the raw material apomorphine.

FIG. 4 shows the particle size distribution of the raw material apomorphine.

Figure 5:
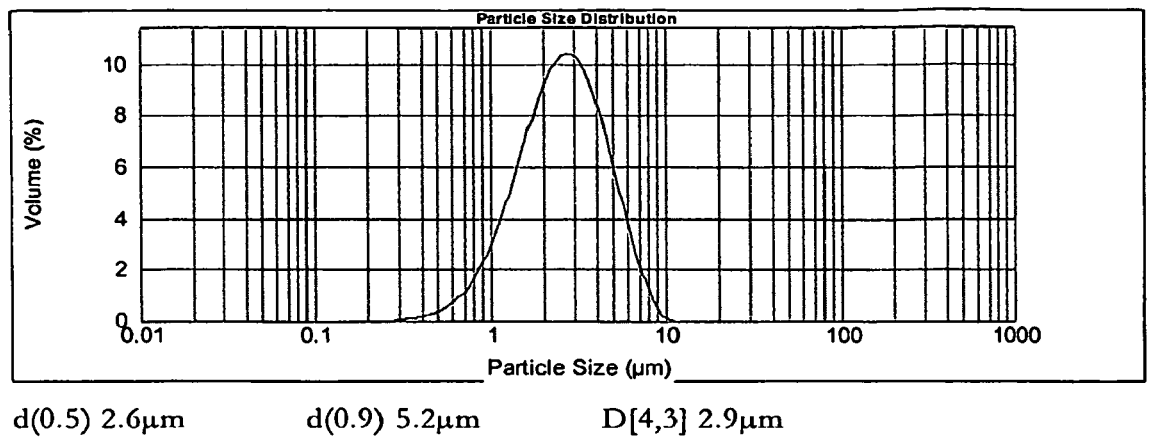
FIG. 5 shows the particle size distribution of the raw material clobozam.

FIG. 5 shows the particle size distribution of the raw material clobozam.

Figure 6:
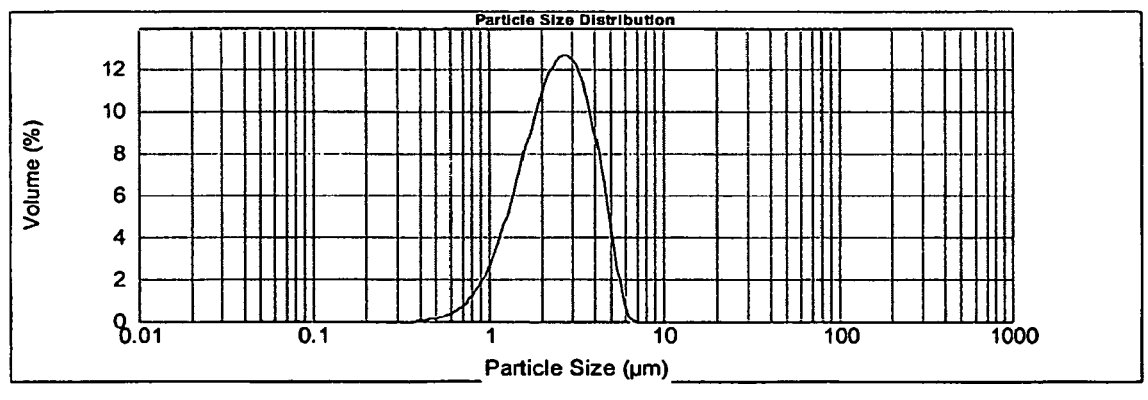
FIG. 6 shows the particle size distribution of the clobozam formulation comprising 95% clobozam and 5% mechano-fused magnesium stearate.

FIG. 6 shows the particle size distribution of the clobozam formulation comprising 95% clobozam and 5% mechanofused magnesium stearate.

Figure 7:
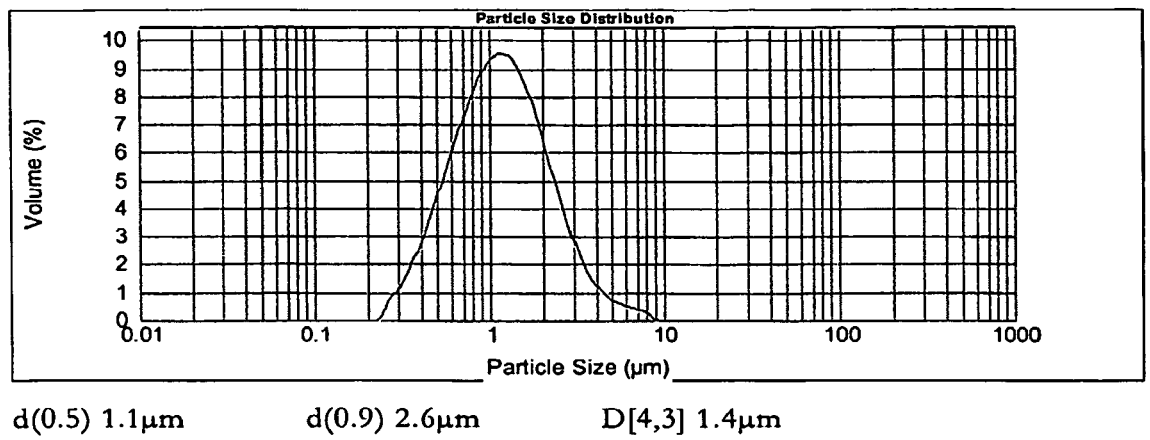
FIG. 7 shows the particle size distribution of the clobozam formulation comprising 95% clobozam and 5% co-jet milled Aerocine.

FIG. 7 shows the particle size distribution of the clobozam formulation comprising 95% clobozam and 5% co-jet milled Aerocine.

Figure 8:
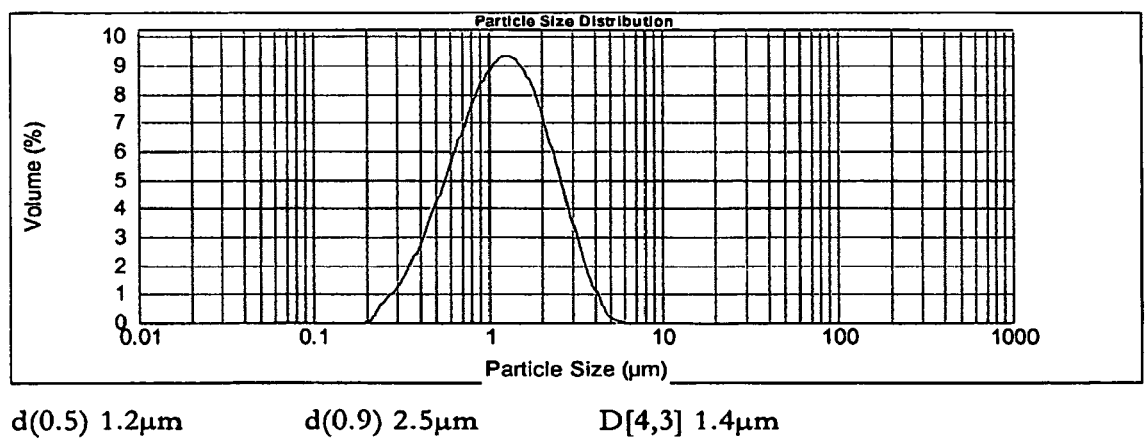
FIG. 8 shows the particle size distribution of the clobozam formulation comprising 95% clobozam and 5% co-jet milled leucine.

FIG. 8 shows the particle size distribution of the clobozam formulation comprising 95% clobozam and 5% co-jet milled leucine.

Figure 9:
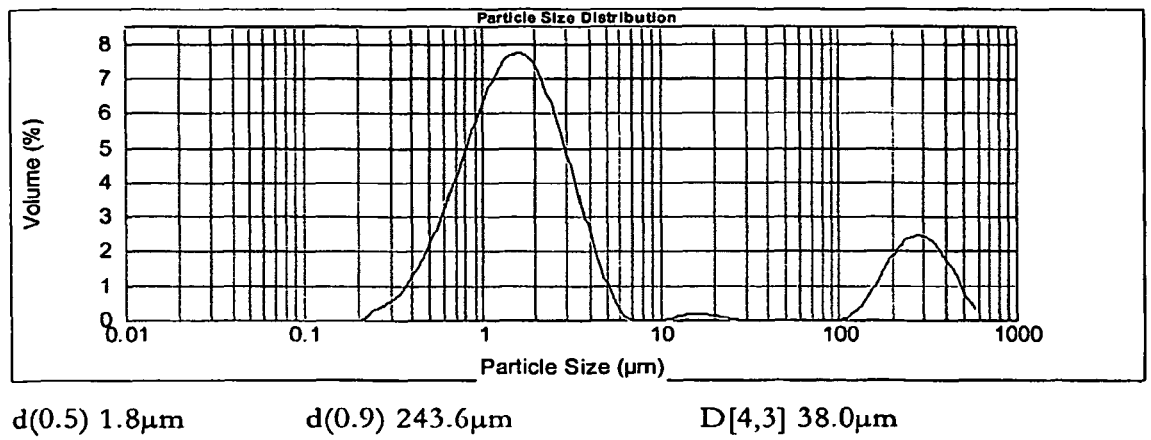
FIG. 9 shows the particle size distribution of the apomorphine formulation comprising 75% lactose, 20% apomorphine and 5% co-jet milled leucine.

FIG. 9 shows the particle size distribution of the apomorphine formulation comprising 75% lactose, 20% apomorphine and 5% co-jet milled leucine.

Figure 10:
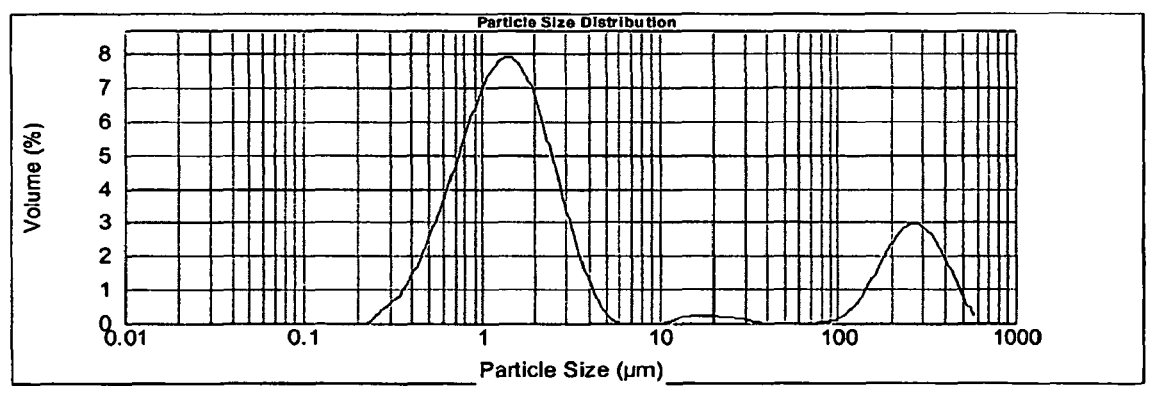
FIG. 10 also shows the particle size distribution of the apomorphine formulation comprising 75% lactose, 20% apomorphine and 5% co-jet milled leucine.

Finally, FIG. 10 also shows the particle size distribution of the apomorphine formulation comprising 75% lactose, 20% apomorphine and 5% co-jet milled leucine.

Where clobozam is co-jet milled with an additive material, a significant drop in particle size is observed. This is not seen for the clobozam mechanofused formulation here.

With the apomorphine-lactose co-milled materials, the size distribution is low (d(50) 1.8 to 1.6), when compared to the particle size distribution of the micronised lactose which comprises 75% of the composition. However, size reduction is not detectable with respect to pure apomorphine, although it should be noted that this comprises only 20% of the powder composition.

In vitro data confirm that, surprisingly, mechanofusion of active particles increased the throat deposition substantially. Mechanofusion has previously been associated with improvement in dispersibility from a passive device, and reduced throat deposition. In this case, mechanofusion with magnesium stearate gives slightly lower throat deposition than mechanofusion with leucine.

The throat deposition appears especially high for mechanofused formulations containing leucine. It is speculated that this could be due to an agglomerating affect during mechanofusion specific to leucine and not magnesium stearate, or an electrostatic effect specific to leucine.

However, surprisingly co-jet milling produces materials which, in comparison, give very low throat deposition, low device deposition and excellent dispersion from an active device. This co-jet milling also produces a significant further size reduction, for example, d(50) changes from about 2.6 μm to about 1 μm for clobozam. When these factors are combined, a remarkable aerosolisation performance is obtained from the in-vitro tests. FPF(ED) are 90 to 96%. This excellent performance was obtained for leucine, Aerocine and magnesium stearate, and for 3 different formulations, including 2 different active agents, with or without lactose diluent.

The consequence of this is the achievement of a very low oropharangeal deposition to the patient, typically of approximately 5%. Given that both throat and upper airway deposition (corresponding to impactor throat and upper impactor stages) is reduced to a minimum, this will also result in a minimised tasteable component, and minimised fraction delivered to the GI tract. This corresponds to a 4-fold reduction in comparison to formulations without additive material.

It was noted that the co-jet milled materials were highly agglomerated in appearance, in contrast to the mechanofused blends, which appeared as more free flowing powders.

Studies suggest that the difference between the performance of the co-jet milled and mechanofused compositions is most apparent when the formulations are dispensed using an active device, such as Aspirair. Video of plume behaviour provided some indication of the reason for differences between the co-jet milled formulations and mechanofused formulations. Mechanofused formulations showed a short fast bolus, whereas co-jet milled formulations showed a more drawn out plume. The "enhanced" flow properties of the mechanofused powders appear to explain their worse Aspirair performance. A degree of powder hold-up within the device appears to be beneficial, allowing a less dense and extended plume to occur.

These video observations suggest the throat deposition difference is related to the powder lifetime within the vortex, with a longer lifetime giving reduced throat deposition. Lower aerosol concentration at the plume front, lower momentum of aerosol plume (with lower cloud density and smaller particle size) and greater opportunity to be de-agglomerated are possible contributors to this improvement. Also, there is also more material in the later, slower part of the plume. Furthermore, lower powder density in the cyclone appears to lead to better dispersion.

It is speculated that the fact that the powder formulations are difficult to extract from the blister actually enhances their delivery characteristics. It slows the extraction of the powder and so the active particles are travelling slower when they are expelled from the dispensing device. This means that the active particles do not travel at the front of the plume of powder created when the device is actuated and this means that the active particles are significantly less likely to impact on the throat of the user. Rather, the active particles are thought to be further back in the plume, which allows them to be inhaled and administered to the lung. Naturally, too much blister retention will be undesirable, as it will result in active agent remaining in the device after actuation.

In general, the co-milling of active particles with additive particles has yielded reduced device/blister retention compared to formulations prepared without additive particles. Mechanofusion was shown to give significantly greater blister retention than co-jet milling. The worst blister retention was seen for mechanofused clobozam with magnesium stearate (13%). This appears related to the dusting nature of such formulations. The mechanofused powders spread and flow more easily, which facilitates higher degrees of contact with the surfaces in bulk powder contact. The co-milled powders however are heavily agglomerated, so contact with surfaces is much reduced, and dust residues are also much less. The device retention also appears greater for mechanofused than co-jet milled powders for clobozam. However, the device retention of apomorphine HCl co-jet milled with leucine appears notably high, at 13%. Device and blister retention does not appear substantially different between the 0.5 and 1.5 bar tests, except for the case of the unaltered pure clobozam, where device retention approaches 50% for the 0.5 bar test.

The tendency of a powder formulation to stick in the blister can be overcome in active devices, where a significant amount of turbulence is created within the blister when the device is actuated. However, this is not the case in a passive device. Therefore, the tendency of a formulation to stick in the blister will have a detrimental effect on the performance of a powder administered using a passive device. That said, as the active particles in the powder dispensed by a passive device are generally not moving as quickly as they would if dispensed by an active device, the problem of throat deposition (usually a result of the active particles travelling at the front of the powder plume) is not so great. Thus, it is clear that the properties of the active particles need to be tailored to the type of device used to dispense the powder.

Tests were carried out to compare the FPF achieved when the co-jet milled compositions are dispensed using passive and active devices. The experiments used a lactose model fired into a TSI. The results were as follows:

TABLE 7

| Formulation | FPF(ED) % | FPF(MD) % (Cyclohaler) | FPF(MD) % (Aspirair) |
|---|---|---|---|
| Micronised lactose | 32 | 18 | — |
| With 5% magnesium stearate (MgSt) in a conventional blender | 35 | 32 | 27 |
| 5% MgSt jet-milled at 2 bar | 68 | 53 | 62 |
| 5% MgSt jet-milled at 7 bar | 52 | 39 | 72 |
| 5% MgSt mechanofused | 69 | 57 | 49 |

This shows that jet milled material which has been co-jet milled at low pressure is better in passive devices whilst high pressure jet milled materials perform better in active devices such as Aspirair.

Co-Jet Milled Clomipramine hydrochloride Formulations in Aspirair Clomipramine hydrochloride was obtained in powdered form. Force control agents leucine and magnesium stearate were used.

Twelve formulations were produced from the original powder, using the Hosokawa AS50 jet mill. Either the pure drug was passed through the mill or a blend of drug with 5% w/w of a force control agent added. The mill was used with a range of parameters. Primarily, these were injector air pressure, grinding air pressure and powder feed rate.

Formulation 14: The pure clomipramine hydrochloride was passed through the microniser three times, each time with an injector air pressure of 8 bar, grinding air pressure of 1.5 bar and powder feed rate of ~1 g/min. Malvern (dry powder) particle size measurement gave a d(50) of 1.2 µm.

Formulation 15: Formulation 14 was pre-blended in a pestle with a spatula with 5% micronised l-leucine. This blend was further micronised with an injector air pressure of 8 bar, grinding air pressure of 1.5 bar and powder feed rate of ~1 g/min. Malvern (dry powder) particle size measurement gave a d(50) of 1.2 µm.

Formulation 16: The pure clomipramine hydrochloride was micronised with an injector air pressure of 7 bar, grinding air pressure of 5 bar and powder feed rate of ~10 g/min. Malvern (dry powder) particle size measurement gave a d(50) of 1.0 µm.

Formulation 17: The pure clomipramine hydrochloride was micronised with an injector air pressure of 7 bar, grinding air pressure of 5 bar and powder feed rate of ~10 g/min. This micronised clomipramine hydrochloride was pre-blended in a pestle with a spatula with 5% micronised l-leucine. This blend was then micronised with an injector air pressure of 7 bar, grinding air pressure of 5 bar and powder feed rate of ~10 g/min. Malvern (dry powder) particle size measurement gave a d(50) of 0.95 µm.

Formulation 18: The pure clomipramine hydrochloride was pre-blended in a pestle with a spatula with 5% magnesium stearate. This blend was micronised with an injector air pressure of 7 bar, grinding air pressure of 5 bar and powder feed rate of ~10 g/min. Malvern (dry powder) particle size measurement gave a d(50) of 0.95 μm.

Formulation 19: The pure clomipramine hydrochloride was micronised with an injector air pressure of 7 bar, grinding air pressure of 1 bar and powder feed rate of ~1 g/min. Malvern (dry powder) particle size measurement gave a d(50) of 1.8 μm.

This pre-micronised clomipramine hydrochloride was then blended in a pestle with a spatula with 5% micronised 1-leucine. This blend was then micronised with an injector air pressure of 7 bar, grinding air pressure of 1 bar and powder feed rate of ~1 g/min. Malvern (dry powder) particle size measurement gave a d(50) of 1.38 μm.

Formulation 20: The pure clomipramine hydrochloride was micronised with an injector air pressure of 7 bar, grinding air pressure of 1 bar and powder feed rate of ~10 g/min. Malvern (dry powder) particle size measurement gave a d(50) of 3.5 μm.

This pre-micronised clomipramine hydrochloride was then blended in a pestle with a spatula with 5% micronised 1-leucine. This blend was then micronised with an injector air pressure of 7 bar, grinding air pressure of 1 bar and powder feed rate of ~10 g/min. Malvern (dry powder) particle size measurement gave a d(50) of 2.0 μm.

Formulation 21: The pure clomipramine hydrochloride was micronised with an injector air pressure of 7 bar, grinding air pressure of 3 bar and powder feed rate of ~1 g/min. Malvern (dry powder) particle size measurement gave a d(50) of 1.2 μm.

This pre-micronised clomipramine hydrochloride was then blended in a pestle with a spatula with 5% micronised 1-leucine. This blend was then micronised with an injector air pressure of 7 bar, grinding air pressure of 3 bar and powder feed rate of ~1 g/min. Malvern (dry powder) particle size measurement gave a d(50) of 0.99 μm.

Formulation 22 The pure clomipramine hydrochloride was micronised with an injector air pressure of 7 bar, grinding air pressure of 3 bar and powder feed rate of ~10 g/min. Malvern (dry powder) particle size measurement gave a d(50) of 1.6 μm.

This pre-micronised clomipramine hydrochloride was then blended in a pestle with a spatula with 5% micronised 1-leucine. This blend was then micronised with an injector air pressure of 7 bar, grinding air pressure of 3 bar and powder feed rate of ~10 g/min. Malvern (dry powder) particle size measurement gave a d(50) of 1.1 μm.

Formulation 23: The clomipramine hydrochloride was pre-blended in a pestle with a spatula with 5% micronised 1-leucine. This blend was micronised with an injector air pressure of 7 bar, grinding air pressure of 5 bar and powder feed rate of ~10 g/min. Malvern (dry powder) particle size measurement gave a d(50) of 1.8 μm.

Formulation 24: The pure clomipramine hydrochloride was micronised with an injector air pressure of 7 bar, grinding air pressure of 5 bar and powder feed rate of ~10 g/min.

This pre-micronised clomipramine hydrochloride was then blended in a pestle with a spatula with 5% magnesium stearate. This blend was then micronised with an injector air pressure of 7 bar, grinding air pressure of 1 bar and powder feed rate of ~10 g/min. Malvern (dry powder) particle size measurement gave a d(50) of 1.38 μm.

Formulation 25: Formulation 24 was then processed in the Hosokawa MechanoFusion Minikit with 1 mm compression gap for 10 minutes. Malvern (dry powder) particle size measurement gave a d(50) of 1.39 μm.

Particle Size Distributions

The Malvern particle size distributions show that clomipramine hydrochloride micronised very readily to small particle sizes. For example, Formulation 16 micronised to 1.0 μm with one pass at the relatively high grinding pressure of 5 bar and the higher powder feed rate of 10 g/min.

Reducing the grinding pressure, for example to 1 bar as with Formulation 19 interim powder, resulted in larger particles (d(50) ~1.8 μm). Intermediate grinding pressure (3 bar) gave an intermediate particle size distribution (d(50) ~1.2 μm as for Formulation 21 interim powder).

Similarly, increasing powder feed rate, for example from 1 to 10 g/min, resulted in larger particles, as can be seen by comparing d(50)s for Formulations 19 and 20.

The addition of an additive material, for example leucine as in Formulation 23, appeared to reduce the milling efficiency. However, this change may have been caused by the concomitant improvement in flowability of the original drug powder leading to a small but significant increase in the powder feed rate into the mill. It was observed in other studies that milling efficiency was increasingly sensitive to this powder feed rate as it increased above 10 g/min.

It appeared possible from this series of examples to design the milling parameters to select a particular d(50). For example, a d(50) of ~1.4 could be obtained either by repeated low pressure milling and low feed rate (Formulation 19) or by a mix of higher and lower pressure milling at a higher feed rate (Formulation 25).

Aspirair Dispersion Performance

Approximately 2 mg of each formulation was then loaded and sealed into a foil blister. This was then fired from an Aspirair device into a Next Generation Impactor with air flow set at 60 l/min. The performance data are summarised in Tables 8, 9 and 10.

TABLE 8

| Formulation | MD (mg) | ED (mg) | FPD (mg) | MMAD |
|---|---|---|---|---|
| 14 (pure drug, jet milled at 8/1.5 bar) | 1.64 | 1.19 | 1.05 | 1.53 |
| 15 (5% leucine, jet-milled at 8/1.5 bar) | 1.55 | 1.32 | 1.19 | 1.68 |
| 16 (pure drug, jet-milled at 7/5 bar) | 2.414 | 1.832 | 1.493 | 1.80 |
| 17 (5% leucine, jet-milled at 7/5 bar) | 2.120 | 1.624 | 1.474 | 1.52 |
| 18 (5% MgSt, jet-milled at 7/5 bar) | 1.737 | 1.519 | 1.390 | 1.44 |
| 19 (5% leucine, jet-milled at 7/1 bar) | 2.031 | 1.839 | 1.550 | 1.90 |
| 20 (5% leucine, jet-milled at 7/1 bar) | 1.821 | 1.685 | 1.071 | 2.44 |
| 21 (5% leucine, jet-milled at 7/3 bar) | 1.846 | 1.523 | 1.437 | 1.61 |
| 22 (5% leucine, jet-milled at 7/3 bar) | 2.213 | 1.940 | 1.733 | 1.72 |
| 23 (5% leucine, single pass at 7/5 bar) | 1.696 | 1.557 | 1.147 | 2.13 |
| 24 (5% MgSt, jet-milled at 7/5 bar & mechanofused) | 1.743 | 1.542 | 1.274 | 1.82 |
| 25 (5% MgSt, jet-milled at 7/5 bar) | 1.677 | 1.570 | 1.351 | 1.72 |

TABLE 9

| Formulation | FPF % (<5 μm) | FPF % (<3 μm) | FPF % (<2 μm) | FPF % (<1 μm) |
|---|---|---|---|---|
| 14 (pure drug, jet milled at 8/1.5 bar) | 88 | 83 | 65 | 21 |
| 15 (5% leucine, jet-milled at 8/1.5 bar) | 90 | 82 | 60 | 17 |
| 16 (pure drug, jet-milled at 7/5 bar) | 82 | 71 | 51 | 14 |
| 17 (5% leucine, jet-milled at 7/5 bar) | 91 | 85 | 68 | 21 |
| 18 (5% MgSt, jet-milled at 7/5 bar) | 91 | 90 | 73 | 20 |
| 19 (5% leucine, jet-milled at 7/1 bar) | 84 | 74 | 48 | 10 |
| 20 (5% leucine, jet-milled at 7/1 bar) | 64 | 46 | 28 | 6 |
| 21 (5% leucine, jet-milled at 7/3 bar) | 94 | 88 | 67 | 14 |
| 22 (5% leucine, jet-milled at 7/3 bar) | 89 | 80 | 56 | 14 |
| 23 (5% leucine, single pass at 7/5 bar) | 74 | 57 | 37 | 9 |
| 24 (5% MgSt, jet-milled at 7/5 bar & mechanofused) | 83 | 68 | 47 | 15 |
| 25 (5% MgSt, jet-milled at 7/5 bar) | 86 | 74 | 53 | 21 |

TABLE 10

| Formulation | Recovery % | Throat % | Blister % | Device % |
|---|---|---|---|---|
| 14 (pure drug, jet milled at 8/1.5 bar) | 82 | 8 | 1 | 26 |
| 15 (5% leucine, jet-milled at 8/1.5 bar) | 81 | 7 | 0 | 15 |
| 16 (pure drug, jet-milled at 7/5 bar) | 121 | 10 | 3 | 21 |
| 17 (5% leucine, jet-milled at 7/5 bar) | 106 | 5 | 1 | 23 |
| 18 (5% MgSt, jet-milled at 7/5 bar) | 91 | 6 | 0 | 12 |
| 19 (5% leucine, jet-milled at 7/1 bar) | 107 | 10.6 | 1.3 | 8.2 |
| 20 (5% leucine, jet-milled at 7/1 bar) | 96 | 24 | 1.3 | 6.1 |
| 21 (5% leucine, jet-milled at 7/3 bar) | 97 | 3 | 0.6 | 16.9 |
| 22 (5% leucine, jet-milled at 7/3 bar) | 116 | 7 | 0.6 | 16.9 |
| 23 (5% leucine, single pass at 7/5 bar) | 87 | 18 | 2 | 6 |
| 24 (5% MgSt, jet-milled at 7/5 bar & mechanofused) | 92 | 14 | 1 | 10 |
| 25 (5% MgSt, jet-milled at 7/5 bar) | 87 | 10 | 1 | 6 |

The device retention appeared high (above 20%) where pure drug was used, and especially increased with small particle sizes (especially 1 μm and below): for example Formulations 14 and 16 had high drug retention. Device retention was lower with use of magnesium stearate, for example as with Formulation 18 where device retention was 12% despite a d(50) of 0.95 μm. Device retention was also reduced below 20% when leucine was used in combination with a particle size above 1 μm, for example with Formulation 22.

Throat deposition was reduced proportionately as particle size was reduced. High throat deposition (>20%) occurs with particle size d(50)>2 μm: e.g. Formulation 20. Throat deposition of below 10% was seen for particle sizes below 1 μm. The reduced inertial behaviour of the smaller particles may well contribute to this observation. However, as noted above, device retention tended to be greater for such small particles.

It is argued that as particle size was reduced, increased adhesiveness and cohesiveness results in increased device retention. This adhesiveness and cohesiveness and hence device retention can be reduced by addition of force control agents, attached to the drug particle surface (or drug and excipient particle surfaces, as appropriate). As argued previously for the apomorphine and clobozam examples, and demonstrated by the video study, in Aspirair it is believed that a level of adhesiveness and cohesiveness is desirable to prolong lifetime in the vortex, yielding a slower plume, but adhesiveness and cohesiveness should not be so high as to result in high device retention. Consequently a balance of particle size, adhesiveness and cohesiveness is required to achieve an optimum performance in Aspirair. The examples contained herein indicate how such a balance may be achieved. This balance may require modifying for each particular different material characteristic.

Single step co-milling with a force control agent appears effective in some examples such as Formulation 18. Multiple stage processing may be more effective, for example, where the conditions are selected to achieve particularly desirable effects. For example, first stage high pressure milling of pure drug may be used to produce the required size distribution (i.e. ~1.4 μm), and a second stage lower pressure co-milling used to mix in the force control agent, whereby better mixing is achieved without milling and with reduced segregation of components in the mill. Such is shown in Formulation 25, where a combination of both relatively low throat deposition and low device retention are achieved.

The results of jet milling heparin with an FCA are set out below.

TABLE 10

| Formulation | d(10) | d(50) | d(60) | d(90) | FPD <5 μm |
|---|---|---|---|---|---|
| Jet milled heparin + leucine (1x) | 0.85 | 3.4 | 4.2 | 8.8 | 20.4 |
| Jet milled heparin + leucine (2x) | 0.95 | 3.5 | 4.1 | 7.0 | 37.1 |
| Jet milled heparin + leucine (3x) | 1.1 | 2.8 | 3.3 | 5.5 | 41.0 |
| Jet milled pure heparin (2x) | | | | | 7.0 |

The combination of heparin and leucine (95:5) was air jet milled using a Hosokawa Micron AS50 mill. The material was passed up to three times through the mill. The powder was then filled into capsules at 20 mg, and then fired from a Monohaler into a twin stage impinger to give a resulting FPF(MD). The powder was also analysed by Malvern particle sizer, and the results are summarised in the table. Pure heparin powder was air jet milled with two passes and gave an FPF(MD) of only 7%.

The optimum amount of additive material will depend on the chemical composition and other properties of the additive material and upon the nature of the active material and/or excipient material, if present. In general, the amount of additive material in the composite active particles will be not more than 60% by weight, based on the weight of the active material and any excipient material. However, it is thought that for most additive materials the amount of additive material should be in the range of 40% to 0.25%, preferably 30% to 0.5%, more preferably 20% to 2%, based on the total weight of the additive material and the active material being milled. In general, the amount of additive material is at least 0.01% by weight based on the weight of the active material.

Clearly, many different designs of jet mills exist and any of these may be used in the present invention. For example, in addition to the AS50 Spiral jet mill and the MC50 Hosakawa Micron used in the experiments discussed above, one can also use other spiral jet mills, pancake jet mills or opposed fluid bed jet mills. The feed rate for the jet mills will depend on their size. Small spiral jet mills might use a feed rate of, for example, 1 to 2 g per minute, whilst industrial scale mills will have a feed rate in the order of kilograms per hour.

The properties of the co-jet milled particles produced using the present invention may, to an extent, be tailored or adjusted by making changes to the jet milling apparatus. For example, the degree of particle coating and particle size reduction may be adjusted by changing the number of jets which are used in the apparatus, and/or by adjusting their orientation, that is, the angles at which they are positioned.

The invention claimed is:

1. A method for making composite active particles for use in a pharmaceutical composition for pulmonary inhalation, the method comprising:

milling an additive material particles to yield particles of milled additive material;

jet milling active particles to yield jet-milled active particles; and co-jet milling the jet-milled active particles in the presence of the particles of milled additive material and, optionally, air or a compressible gas or fluid, wherein the additive material comprises a metal stearate.

2. The method of claim 1, wherein the additive material further comprises at least one material selected from the group consisting of an amino acid and a phospholipid.

3. The method of claim 2, wherein the additive material comprises one or more amino acids selected from the group consisting of leucine, isoleucine, lysine, valine, methionine, and phenylalanine.

4. The method of claim 3, wherein the additive material comprises leucine.

5. The method of claim 2, wherein the additive material comprises magnesium stearate.

6. The method of claim 2, wherein the additive material comprises lecithin.

7. The method of claim 1, wherein the jet milling of the active particles and the co-jet milling of the jet-milled active particles and the particles of the additive material are carried out at an inlet pressure of between 0.1 and 3 bar.

8. The method of claim 1, wherein the jet milling of the active particles and the co-jet milling of the jet-milled active particles and the particles of the additive material are carried out at an inlet pressure of between 3 and 12 bar.

9. The method of claim 1, wherein at least 90% by volume of the active particles are less than 20 μm prior to jet milling, and wherein at least 90% by volume of the jet-milled active particles are less than 20 μm prior to co-jet milling.

10. The method of claim 1, wherein at least 90% by volume of the additive particles are less than 20 μm prior to co-jet milling.

11. The method of claim 1, wherein jet milling of the active particles and the co-jet milling of the jet-milled active particles and the particles of the additive material are carried out at a temperature below room temperature.

12. The method of claim 1, wherein jet milling of the active particles and the co-jet milling of the jet-milled active particles and the particles of the additive material are carried out at a temperature below 10° C.

13. The method of claim 1, wherein the step of co-jet milling the jet-milled active particles and the particles of the additive material further comprises co-jet milling carrier particles with the jet-milled active particles and the particles of the additive material.

14. The method of claim 13, wherein the carrier particles have a particle size of at least 20 μm.

15. The method of claim 13, wherein the carrier particles have a particle size of less than 30 μm.

* * * * *